(12) United States Patent
Ise et al.

(10) Patent No.: US 8,247,091 B2
(45) Date of Patent: Aug. 21, 2012

(54) PLATINUM COMPLEX COMPOUND AND ORGANIC ELECTROLUMINESCENT DEVICE

(75) Inventors: Toshihiro Ise, Kanagawa (JP); Tatsuya Igarashi, Tokyo (JP); Ikuo Kinoshita, Minami-Ashigara (JP); Takeshi Murakami, Minami-Ashigara (JP)

(73) Assignee: Fujifilm Corporation, Tokyo (JP)

( * ) Notice: Subject to any disclaimer, the term of this patent is extended or adjusted under 35 U.S.C. 154(b) by 9 days.

(21) Appl. No.: 13/153,687

(22) Filed: Jun. 6, 2011

(65) Prior Publication Data

US 2011/0234090 A1 Sep. 29, 2011

Related U.S. Application Data

(63) Continuation of application No. 11/815,802, filed as application No. PCT/JP2006/305765 on Mar. 16, 2006, now Pat. No. 7,981,524.

(30) Foreign Application Priority Data

| Mar. 16, 2005 | (JP) | 2005-075340 |
| Mar. 16, 2005 | (JP) | 2005-075341 |
| Jun. 10, 2005 | (JP) | 2005-171031 |

(51) Int. Cl.
*H01L 51/54* (2006.01)
*C09K 11/06* (2006.01)

(52) U.S. Cl. ........ 428/690; 428/917; 313/504; 313/506; 252/301.16; 257/40; 257/E51.044; 546/4

(58) Field of Classification Search ........................ None
See application file for complete search history.

(56) References Cited

U.S. PATENT DOCUMENTS

| 6,303,238 | B1 | 10/2001 | Thompson et al. |
| 2005/0260445 | A1 | 11/2005 | Walters et al. |
| 2006/0202197 | A1 | 9/2006 | Nakayama et al. |
| 2006/0222887 | A1 | 10/2006 | Okada |

FOREIGN PATENT DOCUMENTS

| JP | 2002-175884 A | 6/2002 |
| JP | 2003-272861 A | 9/2003 |
| WO | 00/57676 A1 | 9/2000 |
| WO | 2004/108857 A1 | 12/2004 |

OTHER PUBLICATIONS

Japanese Office Action dated Aug. 26, 2009 in the corresponding Japanese patent application, JP-A-2005-075340.
Japanese Office Action dated Aug. 26, 2009 in the corresponding Japanese patent application, JP-A-2006-072968.
Herrmann et al, "N-Heterocyclic Carbenes" Angew. Chem. Int. Ed. 1997, vol. 36, No. 20, pp. 2163-2187.

*Primary Examiner* — Jennifer Chriss
*Assistant Examiner* — Michael H Wilson
(74) *Attorney, Agent, or Firm* — Sughrue Mion, PLLC

(57) ABSTRACT

An organic electroluminescent device is provided and has at least one organic layer between a pair of electrodes. The organic compound contains a compound represented by the following formula (I):

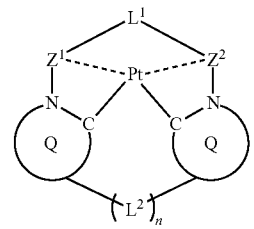

$Z^1$ and $Z^2$ each represents a nitrogen-containing aromatic 6-membered ring coordinating to platinum atom at the nitrogen atom, Q represents a nitrogen-containing aromatic 5-membered ring having one or two nitrogen atoms, $L^1$ and $L^2$ each represents a single bond or a divalent group, and n represents 0 or 1.

5 Claims, No Drawings

PLATINUM COMPLEX COMPOUND AND ORGANIC ELECTROLUMINESCENT DEVICE

CROSS REFERENCE TO RELATED APPLICATION

This application is a continuation application of U.S. application Ser. No. 11/815,802 filed on Aug. 8, 2007 (now allowed), which is a National Stage Application of PCT/JP2006/305765 filed on Mar. 16, 2006, which claims priority from JP 2005-075340 filed on Mar. 16, 2005, JP 2005-075341 filed on Mar. 16, 2005, and JP 2005-171031 filed on Jun. 10, 2005. The entire disclosures of the prior applications are considered part of the disclosure of the accompanying continuation application, and are hereby incorporated by reference.

TECHNICAL FIELD

The present invention relates to a platinum complex compound useful as a light-emitting material and to an organic electroluminescent device using the same.

BACKGROUND ART

An organic electroluminescent device can be driven at a low voltage to provide highly bright luminescence, and hence research and development thereon has actively been made. The organic electroluminescent device has an organic layer sandwiched between a pair of electrodes, wherein an electron injected from the cathode and a hole injected from the anode recombine to generate an exciton, the energy of exciton being utilized for luminescence.

In recent years, luminescence efficiency of the device has been increased by using a phosphorescent material. As light-emitting materials, there have been known iridium complexes or platinum complexes (see, for example, U.S. Pat. No. 6,303,238 and WO 00/57676 pamphlet). However, there have not been developed an element that can show both a high luminescent efficiency and a high durability. Thus, development of a light-emitting material (preferably a phosphorescent material) that can show both a high luminescent efficiency and a high durability has been desired.

DISCLOSURE OF THE INVENTION

An object of an illustrative, non-limiting embodiment of the invention is to provide a complex compound suitable as a light-emitting material and to provide an organic electroluminescent device showing a high luminescent efficiency and a high durability.

As a result of investigations to solve the above-described problems, the inventors have found that an organic EL element containing a quadridentate complex having a specific structure can solve the problems. That is, the invention is achieved by the following means.

(1) A compound represented by formula (IIA):

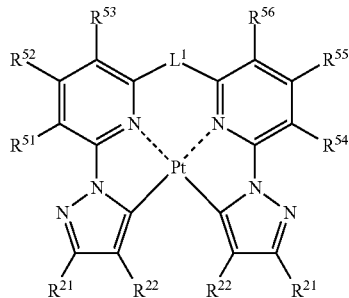

wherein $L^1$ represents a single bond or a divalent linking group, and $R^{21}$, $R^{22}$, $R^{51}$, $R^{52}$, $R^{53}$, $R^{54}$, $R^{55}$ and $R^{56}$ each independently represents a hydrogen atom or a substituent.

(2) The compound as described in (1), wherein the formula (IIA) is represented by formula (IIB):

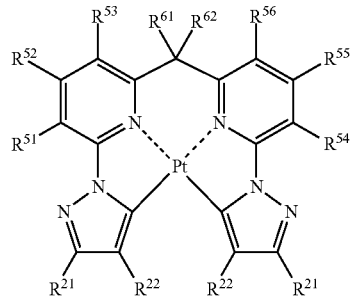

wherein $R^{21}$, $R^{22}$, $R^{51}$, $R^{52}$, $R^{53}$, $R^{54}$, $R^{55}$, $R^{56}$, $R^{61}$ and $R^{62}$ each independently represents a hydrogen atom or a substituent.

(3) The compound as described in (2), wherein the formula (IIB) is represented by formula (IIC):

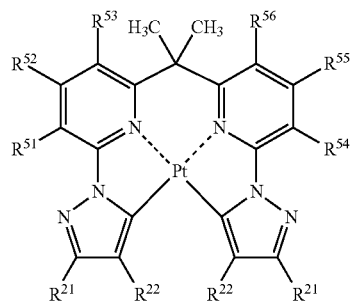

wherein $R^{21}$, $R^{22}$, $R^{51}$, $R^{52}$, $R^{53}$, $R^{54}$, $R^{55}$ and $R^{56}$ each independently represents a hydrogen atom or a substituent.

(4) The compound as described in (3), wherein the formula (IIC) is represented by formula (IID):

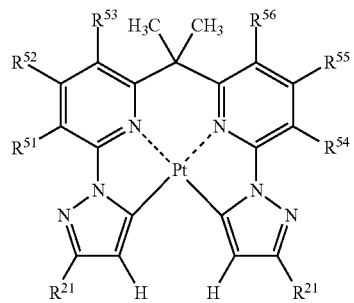

wherein $R^{51}$, $R^{52}$, $R^{53}$, $R^{54}$, $R^{55}$ and $R^{56}$ each independently represents a hydrogen atom or a substituent, and $R^{21}$ represents a substituent.

(5) The compound as described in (4), wherein $R^{51}$, $R^{53}$, $R^{54}$ and $R^{56}$ each represents a hydrogen atom.

(6) The compound as described in any one of (1) to (4), wherein the substituent is a substituent selected from the group consisting of an alkyl group containing from 1 to 20 carbon atoms, an alkenyl group containing from 2 to 10 carbon atoms, an aryl group containing from 6 to 20 carbon atoms, an amino group containing from 0 to 20 carbon atoms, an alkoxy group containing from 1 to 20 carbon atoms, an aryloxy group containing from 6 to 20 carbon atoms, an acyl group containing from 1 to 20 carbon atoms, an alkoxycarbonyl group containing from 2 to 20 carbon atoms, an alkylthio group containing from 1 to 20 carbon atoms, a sulfonyl group containing from 1 to 20 carbon atoms, a hydroxyl group, a halogen atom, a cyano group, a nitro group and a 5- to 7-membered hetero ring group.

(7) An organic electroluminescent device comprising:
a pair of electrodes; and
at least one organic layer between the pair of electrodes, the at least one organic layer containing a compound represented by formula (I):

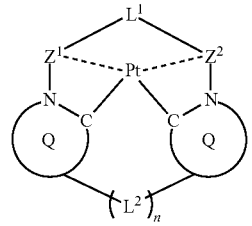

wherein $Z^1$ and $Z^2$ each independently represents a nitrogen-containing aromatic 6-membered ring coordinating to platinum atom at the nitrogen atom thereof, Q represents a nitrogen-containing aromatic 5-membered ring having one or two nitrogen atoms, $L^1$ and $L^2$ each independently represents a single bond or a divalent group, and n represents 0 or 1.

(8) The organic electroluminescent device as described in (7), wherein the formula (I) is represented by formula (II):

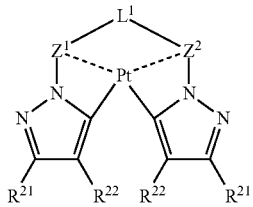

wherein $Z^1$, $Z^2$ and $L^1$ are the same as defined with respect to the formula (I), and $R^{21}$ and $R^{22}$ each independently represents a hydrogen atom or a substituent.

(9) The organic electroluminescent device as described in (7), wherein the formula (I) is represented by formula (III):

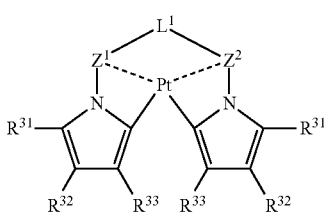

wherein $Z^1$, $Z^2$ and $L^1$ are the same as defined with respect to the formula (I), and $R^{31}$, $R^{32}$ and $R^{33}$ each independently represents a hydrogen atom or a substituent.

(10) The organic electroluminescent device as described in (7), wherein the formula (I) is represented by formula (IV):

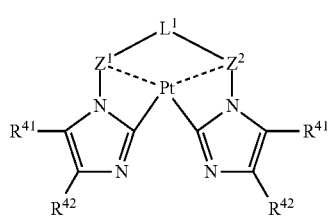

wherein $Z^1$, $Z^2$ and $L^1$ are the same as defined with respect to the formula (I), and $R^{41}$ and $R^{42}$ each independently represents a hydrogen atom or a substituent.

(11) The organic electroluminescent device as described in (8), wherein the formula (II) is represented by formula (IIA):

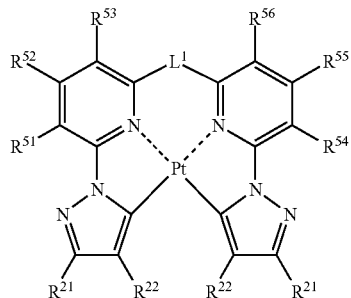

wherein $L^1$ represents a single bond or a divalent linking group, and $R^{21}$, $R^{22}$, $R^{51}$, $R^{52}$, $R^{53}$, $R^{54}$, $R^{55}$ and $R^{56}$ each independently represents a hydrogen atom or a substituent.

(12) The organic electroluminescent device as described in (11), wherein the formula (IIA) is represented by formula (IIB):

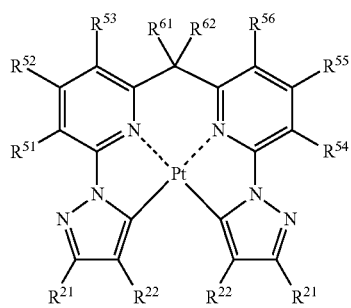

wherein $R^{21}$, $R^{22}$, $R^{51}$, $R^{52}$, $R^{53}$, $R^{54}$, $R^{55}$, $R^{56}$, $R^{61}$ and $R^{62}$ each independently represents a hydrogen atom or a substituent.

(13) The organic electroluminescent device as described in (12), wherein the formula (IIB) is represented by formula (IIC):

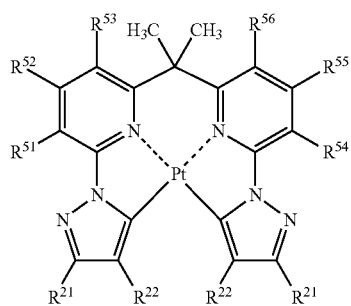

wherein $R^{21}$, $R^{22}$, $R^{51}$, $R^{52}$, $R^{53}$, $R^{54}$, $R^{55}$ and $R^{56}$ each independently represents a hydrogen atom or a substituent.

(14) The organic electroluminescent device as described in (13), wherein the formula (IIC) is represented by formula (IID):

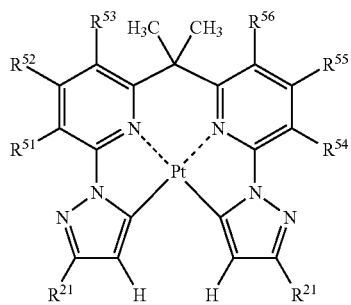

wherein $R^{51}$, $R^{52}$, $R^{53}$, $R^{54}$, $R^{55}$ and $R^{56}$ each independently represents a hydrogen atom or a substituent, and $R^{21}$ represents a substituent.

(15) The organic electroluminescent device as described in (7), wherein the formula (I) is represented by formula (V):

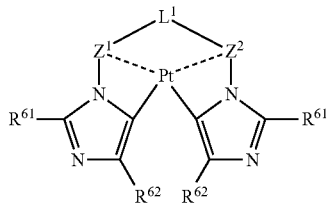

wherein $Z^1$, $Z^2$ and $L^1$ are the same as defined with respect to the formula (I), and $R^{61}$ and $R^{62}$ each independently represents a hydrogen atom or a substituent.

(16) The organic electroluminescent device as described in any one of (8) to (15), wherein the substituent is a substituent selected from the group consisting of an alkyl group containing from 1 to 20 carbon atoms, an alkenyl group containing from 2 to 10 carbon atoms, an aryl group containing from 6 to 20 carbon atoms, an amino group containing from 0 to 20 carbon atoms, an alkoxy group containing from 1 to 20 carbon atoms, an aryloxy group containing from 6 to 20 carbon atoms, an acyl group containing from 1 to 20 carbon atoms, an alkoxycarbonyl group containing from 2 to 20 carbon atoms, an alkylthio group containing from 1 to 20 carbon atoms, a sulfonyl group containing from 1 to 20 carbon atoms, a hydroxyl group, a halogen atom, a cyano group, a nitro group and a 5- to 7-membered hetero ring group.

An organic electroluminescent device (also referred to as "element of the invention" in this specification) can be provided by incorporating a complex of the invention represented by the formulae (I) to (IV), and (IIA) to (IID) (also referred to as "complex of the invention" in this specification) in an organic layer, which shows a high luminescent efficiency (for example, external quantum effect) and shows an excellent durability. Also, by using a compound (complex) having a specific structure, an element can be provided which emits light with a high external quantum effect in the blue region and which has an excellent durability.

DETAILED DESCRIPTION OF THE INVENTION

In this specification, substituent group A is defined as follows.
(Substituent Group A)
There are illustrated an alkyl group (containing preferably from 1 to 30 carbon atoms, more preferably from 1 to 20 carbon atoms, particularly preferably from 1 to 10 carbon atoms; e.g., methyl, ethyl, isopropyl, tert-butyl, n-octyl, n-decyl, n-hexadecyl, cyclopropyl, cyclopentyl or cyclohexyl), an alkenyl group (containing preferably from 2 to 30 carbon atoms, more preferably from 2 to 20 carbon atoms, particularly preferably from 2 to 10 carbon atoms; e.g., vinyl, allyl, 2-butenyl or 3-pentenyl), an alkynyl group (containing preferably from 2 to 30 carbon atoms, more preferably from 2 to 20 carbon atoms, particularly preferably from 2 to 10 carbon atoms; e.g., propargyl or 3-pentynyl), an aryl group (containing preferably from 6 to 30 carbon atoms, more preferably from 6 to 20 carbon atoms, particularly preferably from 6 to 12 carbon atoms; e.g., phenyl, p-methylphenyl, naphthyl or anthranyl), an amino group (containing preferably from 0 to 30 carbon atoms, more preferably from 0 to 20 carbon atoms, particularly preferably from 0 to 10 carbon atoms; e.g., amino, methylamino, dimethylamino, diethylamino, dibenzylamino, diphenylamino or ditolylamino), an alkoxy group (containing preferably from 1 to 30 carbon atoms, more preferably from 1 to 20 carbon atoms, particularly preferably from 1 to 10 carbon atoms; e.g., methoxy, ethoxy, butoxy or 2-ethylhexyloxy), an aryloxy group (containing preferably from 6 to 30 carbon atoms, more preferably from 6 to 20 carbon atoms, particularly preferably from 6 to 12 carbon atoms; e.g., phenyloxy, 1-naphthyloxy or 2-naphthyloxy), a hetero ring oxy group (containing preferably from 1 to 30 carbon atoms, more preferably from 1 to 20 carbon atoms, particularly preferably from 1 to 12 carbon atoms; e.g., pyridyloxy, pyrazyloxy, pyrimidyloxy or quinolyloxy), an acyl group (containing preferably from 1 to 30 carbon atoms, more preferably from 1 to 20 carbon atoms, particularly preferably from 1 to 12 carbon atoms; e.g., acetyl, benzoyl, formyl or pivaloyl), an alkoxycarbonyl group (containing preferably from 2 to 30 carbon atoms, more preferably from 2 to 20 carbon atoms, particularly preferably from 2 to 12 carbon atoms; e.g., methoxycarbonyl or ethoxycarbonyl), an aryloxycarbonyl group (containing preferably from 7 to 30 carbon atoms, more preferably from 7 to 20 carbon atoms, particularly preferably from 7 to 12 carbon atoms; e.g., phenyloxycarbonyl), an acyloxy group (containing preferably from 2 to 30 carbon atoms, more preferably from 2 to 20 carbon atoms, particularly preferably from 2 to 10 carbon atoms; e.g., acetoxy or benzoyloxy), an acylamino group (containing preferably from 2 to 30 carbon atoms, more preferably from 2 to 20 carbon atoms, particularly preferably from 2 to 10 carbon atoms; e.g., acetylamino or benzoylamino), an alkoxycarbonylamino group (containing preferably from 2 to 30 carbon atoms, more preferably from 2 to 20 carbon atoms, particularly preferably from 2 to 12 carbon atoms; e.g., methoxycarbonylamino), an aryloxycarbonylamino group (containing preferably from 7 to 30 carbon atoms, more preferably from 7 to 20 carbon atoms, particularly preferably from 7 to 12 carbon atoms; e.g., phenyloxycarbonylamino), a sulfonylamino group (containing preferably from 1 to 30 carbon atoms, more preferably from 1 to 20 carbon atoms, particularly preferably from 1 to 12 carbon atoms; e.g., methanesulfonylamino or benzenesulfonylamino), a sulfamoyl group (containing preferably from 0 to 30 carbon atoms, more preferably from 0 to 20 carbon atoms, particularly preferably from 0 to 12 carbon atoms; e.g., sulfamoyl, methylsulfamoyl, dimethylsulfamoyl or phenylsulfamoyl), a carbamoyl group (containing preferably from 1 to 30 carbon atoms, more preferably from 1 to 20 carbon atoms, particularly preferably from 1 to 12 carbon atoms; e.g., carbamoyl, methylcarbamoyl, diethylcarbamoyl or phenylcarbamoyl), an alkylthio group (containing preferably from 1 to 30 carbon atoms, more preferably from 1 to 20 carbon atoms, particularly preferably from 1 to 12 carbon atoms; e.g., methylthio or ethylthio), an arylthio group (containing preferably from 6 to 30 carbon atoms, more preferably from 6 to 20 carbon atoms, particularly preferably from 6 to 12 carbon atoms; e.g., phenylthio), a hetero ring thio group (containing preferably from 1 to 30 carbon atoms, more preferably from 1 to 20 carbon atoms, particularly preferably from 1 to 12 carbon atoms; e.g., pyridylthio, 2-benzimidazolylthio, 2-benzoxazolylthio or 2-benzothiazolylthio), a sulfonyl group (containing preferably from 1 to 30 carbon atoms, more preferably from 1 to 20 carbon atoms, particularly preferably from 1 to 12 carbon atoms; e.g., mesyl or tosyl), a sulfinyl group (containing preferably from 1 to 30 carbon atoms, more preferably from 1 to 20 carbon atoms, particularly preferably from 1 to 12 carbon atoms; e.g., methanesulfinyl or benzenesulfinyl), an ureido group (containing preferably from 1 to 30 carbon atoms, more preferably from 1 to 20 carbon atoms, particularly preferably from 1 to 12 carbon atoms; e.g., ureido, methylureido or phenylureido), a phosphoric acid amido group (containing preferably from 1 to 30 carbon atoms, more preferably from 1 to 20 carbon atoms, particularly preferably from 1 to 12 carbon atoms; e.g., diethylphosphoric acid amido or phenylphosphoric acid amido), a hydroxyl group, a mercapto group, a halogen atom (e.g., a fluorine atom, a chlorine atom, a bromine atom or an iodine atom), a cyano group, a sulfo group, a carboxyl group, a nitro group, a hydroxamic acid group, a sulfino group, a hydrazine group, an imino group, a hetero ring group (containing preferably from 1 to 30 carbon atoms, more preferably from 1 to 12; containing, as a hetero atom, e.g., nitrogen atom, oxygen atom or sulfur atom; specific examples thereof being imidazolyl, pyridyl, quinolyl, furyl, thienyl, piperidyl, morpholino, benzoxazolyl, benzimidazolyl, benzothiazolyl, carbazolyl or azepinyl), a silyl group (containing preferably from 3 to 40 carbon atoms, more preferably from 3 to 30 carbon atoms, particularly preferably from 3 to 24 carbon atoms; e.g., trimethylsilyl or triphenylsilyl), a silyloxy group (containing preferably from 3 to 40 carbon atoms, more preferably from 3 to 30 carbon atoms, particularly preferably from 3 to 24 carbon atoms; e.g., trimethylsilyloxy or triphenylsilyloxy), etc. These substituents may further be substituted.

The substituent group A or the following groups in the formulae (I) to (V), and (IIA) to (IID) to be described hereinafter ($R^{21}$, $R^{22}$, $R^{31}$, $R^{32}$, $R^{33}$, $R^{41}$, $R^{42}$, $R^{51}$, $R^{52}$, $R^{53}$, $R^{54}$, $R^{55}$, $R^{56}$, $R^{61}$ and $R^{62}$) are more preferably a substituent group consisting of the following group (group: an alkyl group containing from 1 to 20 carbon atoms, an alkenyl group containing from 2 to 10 carbon atoms, an aryl group containing from 6 to 20 carbon atoms, an amino group containing from 0 to 20 carbon atoms, an alkoxy group containing from 1 to 20 carbon atoms, an aryloxy group containing from 6 to 20 carbon atoms, an acyl group containing from 1 to 20 carbon atoms, an alkoxycarbonyl group containing from 2 to 20 carbon atoms, an alkylthio group containing from 1 to 20 carbon atoms, a sulfonyl group containing from 1 to 20 carbon atoms, a hydroxyl group, a halogen atom, a cyano group, a nitro group and a 5- to 7-membered hetero ring group, still more preferably an alkyl group containing from 1 to 20 carbon atoms, an aryl group containing from 6 to 20 carbon atoms, an amino group containing from 0 to 20 carbon atoms, an alkoxy group containing from 1 to 20 carbon atoms, an aryloxy group containing from 6 to 20 carbon atoms, an alkylthio group containing from 1 to 20 carbon atoms, a halogen atom, a cyano group and a 5- to 7-membered hetero ring group).

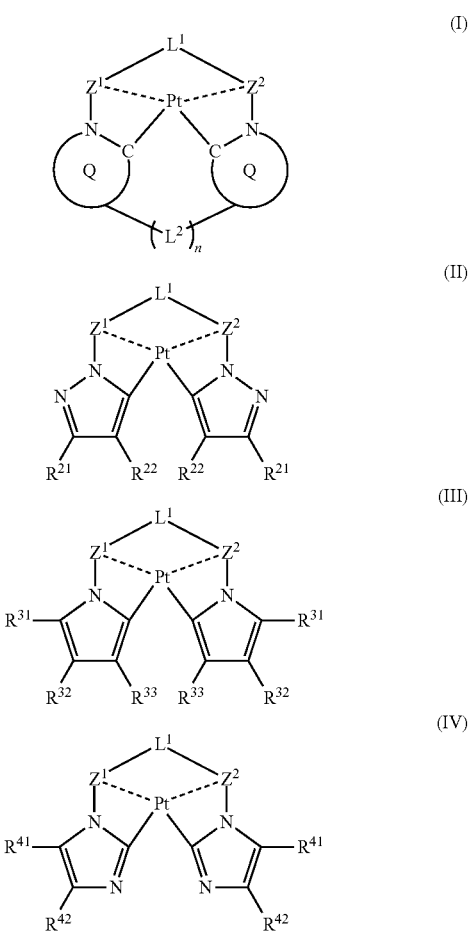

The organic electroluminescent device of the invention (also referred to as "device of the invention" in this specification) will be described in detail below.

The device of the invention has at least one organic layer between a pair of electrodes. The device of the invention has a pair of electrodes (a cathode and an anode) on a substrate, and has the organic layer between the two electrodes. In view of the property of the device, at least one of the anode and the cathode is preferably transparent.

The device of the invention is characterized in that it contains in its organic layer a quadridentate platinum complex of the invention, which is represented by the formula (I) (also referred to as "complex of the invention" in this specification) . The function of the at least one organic layer is not particularly limited, and may have a hole injecting layer, a hole transporting layer, an electron injecting layer, an electron transporting layer, a hole blocking layer, an electron blocking layer, an exciton blocking layer or a protective layer in addition to the light-emitting layer. Also, the device of the invention may have a hole injecting layer, a hole transporting layer, an electron injecting layer, an electron transporting layer, a hole blocking layer, an electron blocking layer, an exciton blocking layer or a protective layer in addition to the at least one organic layer. Each of these layers may also exert the function of other layer.

As an embodiment of the organic layer in the invention, an embodiment is preferred wherein a hole transporting layer, a light-emitting layer and an electron transporting layer are stacked in this order from the anode side. Further, a charge blocking layer may be provided between the hole transporting layer and the light-emitting layer or between the light-emitting layer and the electron transporting layer. A hole injecting layer may be provided between the anode and the hole transporting layer, and an electron injecting layer may be provided between the cathode and the electron transporting layer. Additionally, each layer may be divided into plural secondary layers.

In the case where the organic layer is composed of plural layers, the complex of the invention may be incorporated in any of the layers. The complex of the invention is preferably incorporated in the light-emitting layer and, more preferably, the complex is incorporated in the light-emitting layer as a light-emitting material. It is particularly preferred for the complex to be incorporated in the light-emitting layer together with at least one host material.

In the case of incorporating in the light-emitting layer as a light-emitting material, the content of the complex of the invention is preferably from 0.1% by weight to 50% by weight, more preferably from 0.1% by weight to 40% by weight, still more preferably from 0.2% by weight to 30% by weight, still more preferably from 0.3% by weight to 20% by weight, still further more preferably from 0.5% by weight to 20% by weight, most preferably from 0.5% by weight to 15% by weight, based on the total weight of the layer.

The host material is a compound which mainly perform injection and transportation of charge in the light-emitting layer and which itself substantially does not emit light. The phrase "substantially does not emit light" as used herein in this specification means that the amount of light emitted from the compound which substantially does not emit light is preferably 5% or less, more preferably 3% or less, still more preferably 1% or less, based on the total amount of light emitted from the device.

The concentration of the host material in the light-emitting layer is not particularly limited, but is preferably a major component (component whose content is the largest) in the light-emitting layer, more preferably from 50% by weight to 99.9% by weight, still more preferably from 70% by weight to 99.8% by weight, particularly preferably from 80% by weight to 99.7% by weight, most preferably from 90% by weight to 99.5% by weight.

The glass transition point of the host material is preferably from 100° C. to 500° C., more preferably from 110° C. to 300° C., still more preferably from 120° C. to 250° C.

The wavelength of fluorescence of the host material of the invention in a film state is preferably from 400 nm to 650 nm, more preferably from 420 nm to 600 nm, still more preferably from 440 nm to 550 nm.

As the host material to be used in the invention, those compounds which are described in JP-A-2002-100476, paragraphs 0113 to 0161 and JP-A-2004-214179, paragraphs 0087 to 0098 can preferably be used which, however, are not limitative at all.

The complex represented by the formula (I) will be described below. In the formula (I), $Z^1$ and $Z^2$ each represents a nitrogen-containing 6-membered aromatic ring which coordinates with platinum through its nitrogen atom. Q represents a 5-membered aromatic ring containing one or two nitrogen atoms. $L^1$ and $L^2$ each represents a single bond or a linking group. n represents 0 or 1.

$Z^1$ and $Z^2$ each represents a nitrogen-containing 6-membered aromatic ring which coordinates with platinum through its nitrogen atom. Examples of $Z^1$ and $Z^2$ include pyridine, pyrazine, pyrimidine, pyridazine and triazine, preferred examples thereof include pyridine, pyrazine and pyrimidine, more preferred examples thereof include pyridine and pyrimidine, still more preferred examples thereof include pyridine and pyrazine, and a particularly preferred example thereof is pyridine. $Z^1$ and $Z^2$ may be the same or different from each other. $Z^1$ and $Z^2$ may, if possible, have a substituent selected from the substituent group A.

Preferred examples of the substituent which $Z^1$ and $Z^2$ may have include an alkyl group, an aryl group, an amino group, an alkoxy group, an aryloxy group, an acyl group, an alkoxycarbonyl group, an alkylthio group, a sulfonyl group, a hydroxyl group, a halogen atom, a cyano group, a nitro group and a hetero ring group.

$Z^1$ and $Z^2$ may form, if possible, a condensed ring together with other ring. Examples of the ring to be condensed with include a benzene ring, a pyridine ring, a pyrazine ring, a pyrimidine ring, a pyridazine, a thiophene ring, a furan ring, a pyrrole ring, an imidazole ring, a pyrazole ring, a triazole ring, an oxazole ring, a thiazole ring, an oxadiazole ring and a thiadiazole ring.

Preferred examples of $Z^1$ and $Z^2$ include substituted and unsubstituted pyridine rings, pyrazine rings and pyrimidine rings, more preferred examples thereof include unsubstituted pyridine and pyrazine rings, and a still more preferred example thereof includes an unsubstituted pyridine ring.

Q represents a nitrogen-containing aromatic 5-membered ring containing 1 or 2 nitrogen atom. That is, Q represents a nitrogen-containing aromatic 5-membered ring containing 1 or 2 nitrogen atoms including the carbon atom and the nitrogen atom in the moiety of Z1-N—C—Pt (or Z2-N—C—Pt). Examples of Q include (un)substituted pyrroles, pyrazoles and imidazoles, preferred examples thereof include (un)substituted pyrroles and pyrazoles, more preferred examples thereof include (un)substituted pyrazoles, and still more preferred examples thereof include pyrazoles having a substituent at 3-position, still more preferred examples thereof include pyrazoles having an alkyl group or a cyano group at 3-position, and particularly preferred examples thereof include pyrazoles having a trifluoromethyl group, a t-butyl group or a cyano group at 3-position.

Q may have, if possible, a substituent. The substituent is selected from the substituent group A. Preferred examples of Q include an alkyl group, an aryl group, a hetero ring group and a cyano group, more preferred examples thereof include an alkyl group and a cyano group, and still more preferred examples thereof include a trifluoromethyl group, a t-butyl group and a cyano group.

Q may form, if possible, a condensed ring together with other ring. Examples of the other ring to be condensed with include a benzene ring, a pyridine ring, a pyrazine ring, a pyrimidine ring, a pyridazine ring, a thiophene ring, a furan ring, a pyrrole ring, an imidazole ring, a pyrazole ring, a triazole ring, an oxazole ring, a thiazole ring, an oxadiazole ring and a thiadiazole ring.

$L^1$ and $L^2$ each represents a single bond or a divalent linking group, and n represents 0 or 1, with 0 being preferred. That is, in the case where n=0, two Qs do not connect to each other to form a ring. The divalent linking group is not particularly limited, but is preferably a linking group comprising carbon atom, nitrogen atom, oxygen atom, sulfur atom and/or silicon atom. Specific examples of the divalent linking group are illustrated below which, however, do not limit the invention in any way.

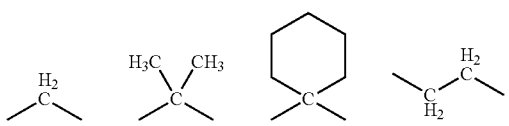

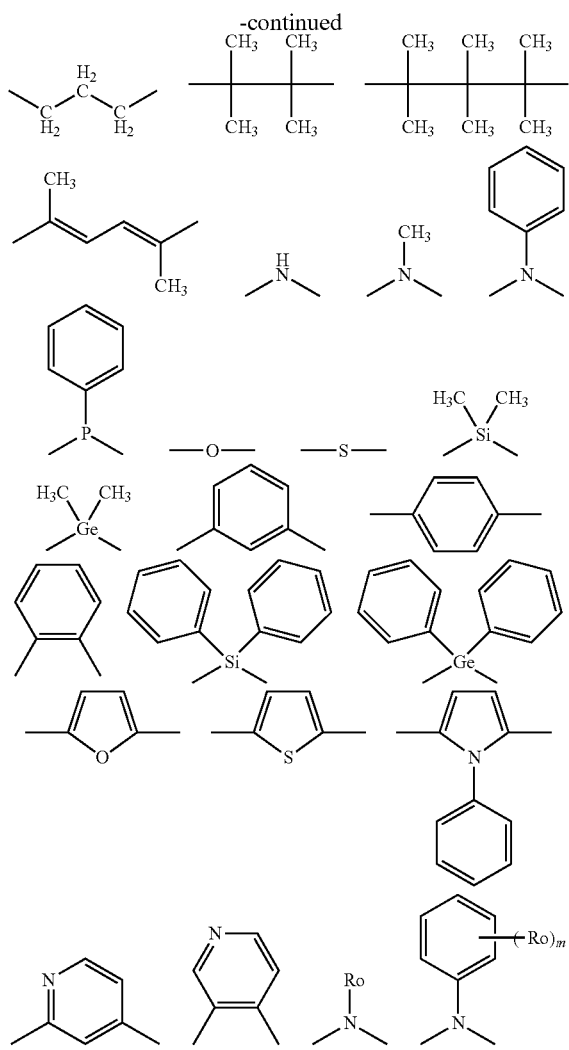

$R_0$ represents a substituent selected from the substituent group A. Preferred examples of $R_0$ include an alkyl group, and more preferred examples thereof include an alkyl group containing from 1 to 6 carbon atoms. m represents an integer of from 1 to 5. m is preferably from 2 to 5, more preferably from 2 to 3.

These linking groups may further have, if possible, a substituent. As the substituent to be introduced, those which have been described as substituents for $Z^1$ and $Z^2$ can be applied.

Preferred examples of $L^1$ include a dialkylmethylene group, a diarylmethylene group and a diheteroarylmethylene group, and more preferred examples thereof include a dimethylmethylene group and a diphenylmethylene group, with a dimethylmethylene group being still more preferred.

$L^2$ is preferably a tetraalkylethylene group, a tetraarylethylene group or a tetraheteroarylethylene group, more preferably a tetraalkylethylene group, and still more preferably a tetramethylethylene group.

Of the complexes represented by the formula (I), one preferred embodiment is a complex represented by the formula (II). In the formula (II), $Z^1$ and $Z^2$ each represents a nitrogen-containing aromatic 6-membered ring coordinating to platinum at the nitrogen atom. $L^1$ represents a single bond or a divalent linking group. $L^1$ is the same as that defined with respect to the formula (I), and the preferred scope thereof is also the same as described there. $R^{21}$ and $R^{22}$ each independently represents a hydrogen atom or a substituent, with the substituent being the same as one of the substituent group A. $R^{21}$ and $R^{22}$ which are connected to the same pyrazole ring may be connected to each other to form a condensed ring. $R^{22}$ may be connected to $R^{22}$ being connected to other pyrazole to form a ring.

Preferred examples of $R^{21}$ include a hydrogen atom, a methyl group, a trifluoromethyl group, a t-butyl group and a cyano group, more preferred examples thereof include a methyl group, a trifluoromethyl group, a t-butyl group or a cyano group, and still more preferred examples thereof include a trifluoromethyl group, a t-butyl group and a cyano group.

$R^{22}$ is preferably a hydrogen atom, a methyl group, a trifluoromethyl group, a t-butyl group or a cyano group, or $R^{22}$s are connected to each other to form a substituted or unsubstituted methylene or ethylene. $R^{22}$ is more preferably a hydrogen atom or a cyano group, or $R^{22}$s are connected to each other to form a substituted or unsubstituted ethylene. $R^{22}$ is still more preferably a hydrogen atom, or $R^{22}$s are connected to each other to form a tetramethyl ethylene. $R^{22}$ is particularly preferably a hydrogen atom.

Of the complexes represented by the formula (I), other preferred embodiment is a complex represented by the formula (III). In the formula (III), $Z^1$ and $Z^2$ each represents a nitrogen-containing aromatic 6-membered ring coordinating to platinum at the nitrogen atom. $L^1$ represents a single bond or a divalent linking group. $L^1$ is the same as that defined with respect to the formula (I), and the preferred scope thereof is also the same as described there. $R^{31}$ and $R^{32}$ each independently represents a hydrogen atom or a substituent, with the substituent being the same as one of the substituent group A. $R^{31}$ and $R^{32}$, $R^{32}$ and $R^{33}$, and $R^{33}$ and another $R^{33}$ of another pyrrole ring may be connected to each other to form a condensed ring.

As a ring forming the condensed ring formed by $R^{31}$ and $R^{32}$, or $R^{32}$ and $R^{33}$, connected to each other, there are illustrated a benzene ring, a pyridine ring, a pyrazine ring, a pyrimidine ring, a pyridazine ring, a pyrrole ring, a pyrazole ring, an imidazole ring, an oxazole ring, a thiazole ring, an isothiazole ring and an isoxazole ring, with a benzene ring, a pyridine ring, a pyrimidine ring and pyrazine ring being preferred. These rings may further be condensed with other ring.

$R^{31}$ is preferably a hydrogen atom, an alkyl group, an aryl group, a cyano group or a group forming a condensed ring together with $R^{32}$, is more preferably a hydrogen atom, a methyl group, a t-butyl group, a phenyl group, a cyano group, a trifluoromethyl group or a group forming a condensed ring together with $R^{32}$, still more preferably a methyl group, a t-butyl group or a group forming a condensed ring together with $R^{32}$.

$R^{32}$ is preferably a hydrogen atom, an alkyl group, an aryl group, a cyano group or a group forming a condensed ring together with $R^{31}$ or $R^{33}$, more preferably a hydrogen atom, a methyl group, a t-butyl group, a phenyl group, a cyano group, a trifluoromethyl group or a group forming a condensed ring together with $R^{31}$ or $R^{33}$, still more preferably a t-butyl group, a cyano group, a trifluoromethyl group or a group forming a condensed ring together with $R^{31}$.

$R^{33}$ is preferably a hydrogen atom, an alkyl group, an aryl group, a cyano group or a group forming a condensed ring together with $R^{32}$, more preferably a hydrogen atom, a methyl group or a group forming a condensed ring together with $R^{32}$, still more preferably a hydrogen atom or a group forming a condensed ring together with $R^{32}$.

Of the complexes represented by the formula (I), other preferred embodiment is a complex represented by the formula (IV). The formula (IV) will be described below. In the formula (IV), $Z^1$ and $Z^2$ each represents a nitrogen-containing aromatic 6-membered ring coordinating to platinum at the nitrogen atom. $L^1$ represents a single bond or a divalent linking group. $L^1$ is the same as that defined with respect to the formula (I), and the preferred scope thereof is also the same as described there. $R^{41}$ and $R^{42}$ each independently represents a hydrogen atom or a substituent. As the substituent, those selected from the substituent group A may be applied. $R^{41}$ and $R^{42}$ may be connected to each other to form a condensed ring. As a ring forming the condensed ring formed by $R^{41}$ and $R^{42}$ connected to each other, there are illustrated a benzene ring, a pyridine ring, a pyrazine ring, a pyrimidine ring, a pyridazine ring, a pyrrole ring, a pyrazole ring, an imidazole ring, an oxazole ring, a thiazole ring, an isothiazole ring and an isoxazole ring, with a benzene ring, a pyridine ring, a pyrimidine ring and pyrazine ring being preferred. These rings may further be condensed with other ring.

$R^{41}$ is preferably a hydrogen atom, an alkyl group, an aryl group, a cyano group or a group forming a condensed ring together with $R^{42}$, more preferably a hydrogen atom, a methyl group, a t-butyl group, a phenyl group, a cyano group, a trifluoromethyl group or a group forming a condensed ring together with $R^{42}$, still more preferably a methyl group, a cyano group or a group forming a condensed ring together with $R^{42}$.

$R^{42}$ is preferably a hydrogen atom, an alkyl group, an aryl group, a cyano group or a group forming a condensed ring together with $R^{41}$, more preferably a hydrogen atom, a methyl group, a t-butyl group, a phenyl group, a cyano group, a trifluoromethyl group or a group forming a condensed ring together with $R^{41}$, still more preferably a methyl group, a cyano group or a group forming a condensed ring together with $R^{41}$.

Of the complexes represented by the formula (I), other preferred embodiment is a complex represented by the formula (V). The formula (V) will be described below. In the formula (V), $Z^1$ and $Z^2$ are the same as those defined with respect to the formula (I) and each represents a nitrogen-containing aromatic 6-membered ring coordinating to platinum at the nitrogen atom, with the preferred scope thereof being also the same as described there. $L^1$ represents a single bond or a divalent linking group. $L^1$ is the same as that defined with respect to the formula (I), and the preferred scope thereof is also the same as described there. $R^{61}$ and $R^{62}$ each independently represents a hydrogen atom or a substituent. As the substituent, those selected from the substituent group A may be applied.

$R^{61}$ is preferably a hydrogen atom, an alkyl group, an aryl group or a cyano group, more preferably a hydrogen atom, a methyl group, a t-butyl group, a phenyl group, a cyano group or a trifluoromethyl group, and still more preferably a cyano group.

$R^{62}$ is preferably a hydrogen atom, an alkyl group, an aryl group or a cyano group, more preferably a hydrogen atom, a methyl group, a t-butyl group, a phenyl group, a cyano group or a trifluoromethyl group, and still more preferably a methyl group or a cyano group.

More preferred complexes among the complexes represented by the formula (II) are those complexes which are represented by the formula (IA). The formula (IIA) will be described below. In the formula (IIA), $L^1$ represents a single bond or a divalent linking group. $L^1$ is the same as that defined with respect to the formula (I), and the preferred scope thereof is also the same as described there. $R^{21}$, $R^{22}$, $R^{51}$, $R^{52}$, $R^{53}$, $R^{54}$, $R^{55}$ and $R^{56}$ each represents a hydrogen atom or a substituent. $R^{21}$ and $R^{22}$ are the same as those defined with respect to the formula (II), and the preferred scope thereof is also the same as described there. $R^{51}$ to $R^{56}$ each represents a hydrogen atom or a substituent. The substituents represented by $R^{51}$ to $R^{56}$ are the same as those of the substituent group A. $R^{51}$ to $R^{56}$ may, if possible, be connected to each other to form a ring.

Preferred examples of $R^{51}$ and $R^{54}$ include a hydrogen atom, an alkyl group, an aryl group, an amino group, an alkoxy group, an aryloxy group, an acyl group, an alkoxycarbonyl group, an alkylthio group, a sulfonyl group, a hydroxyl group, a halogen atom, a cyano group, a nitro group and a hetero ring group, more preferred examples thereof include a hydrogen atom, an alkyl group, an aryl group, a halogen atom, a cyano group and a hetero ring group, still more preferred examples thereof include a hydrogen atom, a methyl group, a t-butyl group, a trifluoromethyl group, a phenyl group, a fluorine atom, a cyano group and a pyridyl group, and yet more preferred examples thereof include a hydrogen atom, a methyl group and a fluorine atom, with a hydrogen atom being particularly preferred.

A preferred scope of $R^{53}$ and $R^{56}$ is the same as the preferred scope of $R^{51}$ and $R^{54}$.

Preferred examples of $R^{52}$ and $R^{55}$ include a hydrogen atom, an alkyl group, an aryl group, an amino group, an alkoxy group, an aryloxy group, an alkylthio group, an arylthio group, a halogen atom, a cyano group and a hetero ring group, more preferred examples thereof include a hydrogen atom, an alkyl group, an aryl group, an amino group, an alkoxy group, an aryloxy group and a hetero ring group, still more preferred examples thereof include a hydrogen atom, an alkyl group, an amino group, an alkoxy group and a hetero ring group, and yet more preferred examples thereof include a hydrogen atom, a methyl group, a t-butyl group, a dimethylamino group, a diphenylamino group, a methoxy group and a carbazolyl group, with a hydrogen atom being particularly preferred.

More preferred complexes among the complexes represented by the formula (IIA) are those complexes which are represented by the formula (IIB). The formula (IIB) will be described below. In the formula (IIB), $R^{21}$, $R^{22}$, $R^{51}$, $R^{52}$, $R^{53}$, $R^{54}$, $R^{55}$, $R^{56}$, $R^{61}$ and $R^{62}$ each represents a hydrogen atom or a substituent. $R^{21}$ and $R^{22}$ are the same as those defined with respect to the formula (II), and the preferred scope thereof is also the same as described there. $R^{51}$ to $R^{56}$ are the same as those defined with respect to the formula (IIA), and the preferred scope thereof is also the same as described there. $R^{61}$ and $R^{62}$ each represents a hydrogen atom or a substituent. The substituents represented by $R^{61}$ and $R^{62}$ are the same as those of the substituent group A. Preferred examples of $R^{61}$ and $R^{62}$ include a hydrogen atom, an alkyl group, an aryl group, a halogen atom, a cyano group and a hetero ring group, still more preferred examples thereof include a hydrogen atom, a methyl group, a trifluoromethyl group, a phenyl group, a fluorine atom, a cyano group and a pyridyl group, and yet more preferred examples thereof include a methyl group, a phenyl group and a pyridyl group, with a methyl group being particularly preferred.

More preferred complexes among the complexes represented by the formula (IIB) are those complexes which are represented by the formula (IIC). The formula (IIC) will be described below. In the formula (IIC), $R^{21}$, $R^{22}$, $R^{51}$, $R^{52}$, $R^{53}$, $R^{54}$, $R^{55}$ and $R^{56}$ each represents a hydrogen atom or a substituent. $R^{21}$ and $R^{22}$ are the same as those defined with respect to the formula (II), and the preferred scope thereof is also the same as described there. $R^{51}$ to $R^{56}$ are the same as those defined with respect to the formula (IIA), and the preferred scope thereof is also the same as described there.

More preferred complexes among the complexes represented by the formula (IIC) are those complexes which are represented by the formula (IID). The formula (IID) will be described below. In the formula (IID), $R^{51}$, $R^{52}$, $R^{53}$, $R^{54}$, $R^{55}$ and $R^{56}$ each represents a hydrogen atom or a substituent. $R^{21}$ represents a substituent. $R^{51}$ to $R^{56}$ are the same as those defined with respect to the formula (IIA), and the preferred scope thereof is also the same as described there. $R^{21}$ represents a substituent. The substituents represented by $R^{23}$ are the same as those of the substituent group A. $R^{21}$ is preferably an alkyl group, an aryl group, an amino group, an alkoxy group, an aryloxy group, an acyl group, an alkoxycarbonyl group, an alkylthio group, a sulfonyl group, a hydroxyl group, a halogen atom, a cyano group, a nitro group or a hetero ring group, still more preferably an alkyl group, an aryl group, a sulfonyl group, a halogen atom, a cyano group or a hetero ring group, still more preferably an alkyl group, a perfluoroalkyl group, an aryl group, a perfluoroaryl group, a sulfonyl group, a halogen atom, a cyan group or a hetero ring group, still more preferably a methyl group, a t-butyl group, a trifluoromethyl group, a phenyl group, a tolyl group, a pentafluorophenyl group, a mesyl group, a tosyl group, a fluorine atom, a cyano group or a pyridyl group, still more preferably a methyl group, a t-butyl group, a trifluoromethyl group or a cyano group, and particularly preferably a t-butyl group, a trifluoromethyl group or a cyano group.

In the formula (IID), $R^{51}$, $R^{53}$, $R^{54}$ and $R^{56}$ preferably represent a hydrogen atom.

Specific examples of the complex of the invention represented by the formula (I) are illustrated below which, however, are not to be construed as limiting the invention. (Additionally, Ph represents a phenyl group, Me represents a methyl group, and tBu represents a tertiary butyl group. A bond line with one end having nothing drawn represents that the end is a methyl group, and a zigzag line with nothing being drawn at the summit represents an unsubstituted methylene group.

1

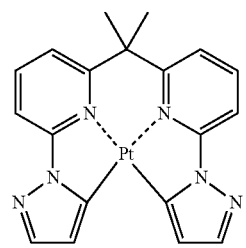

2

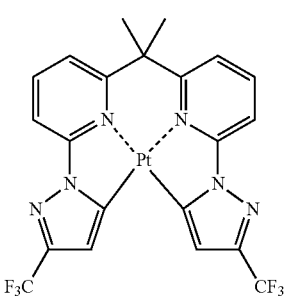

3

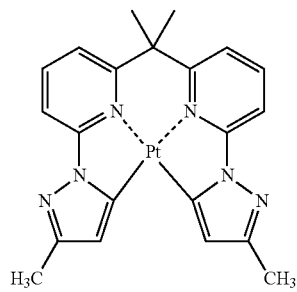

4

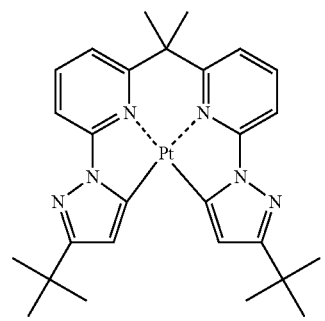

5

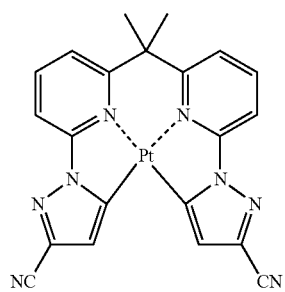

6

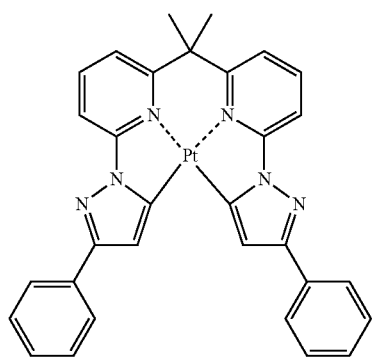

7

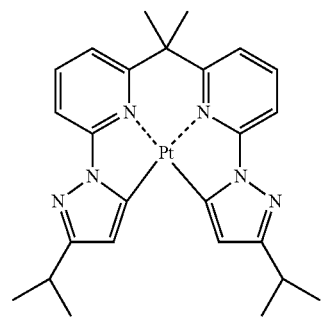

8
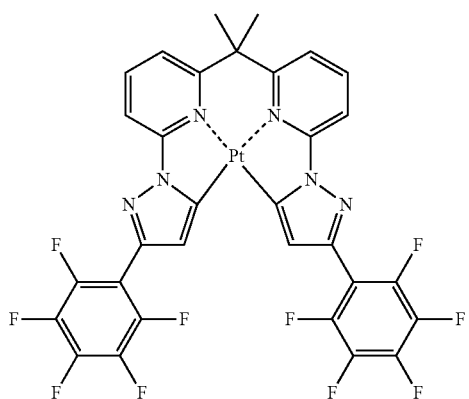
9
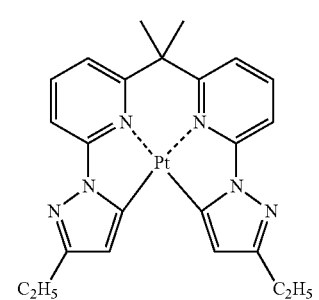
10
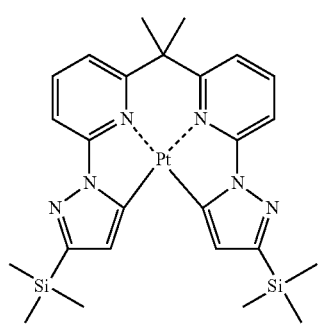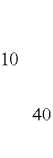
11
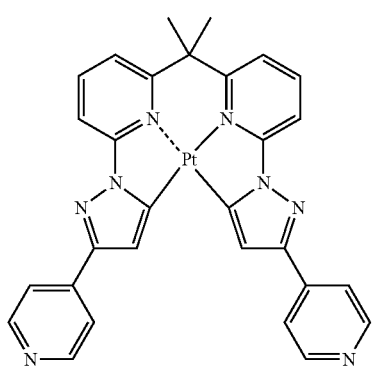
12
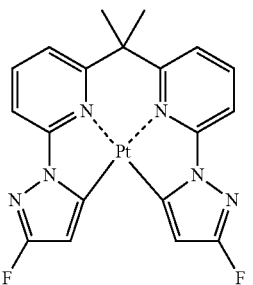
13
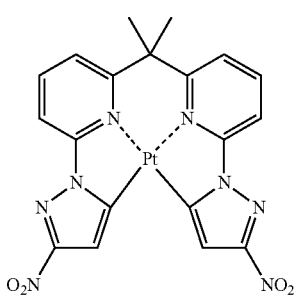
14
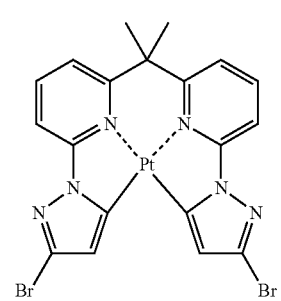
15
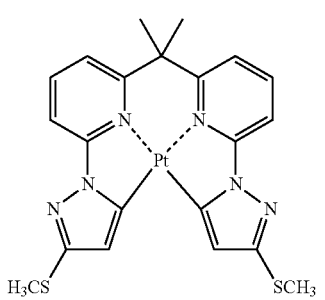
16
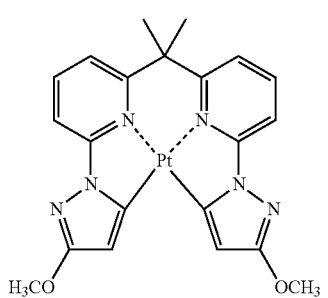

17
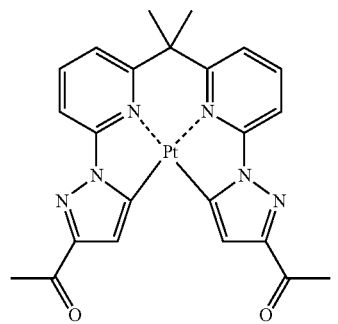
18
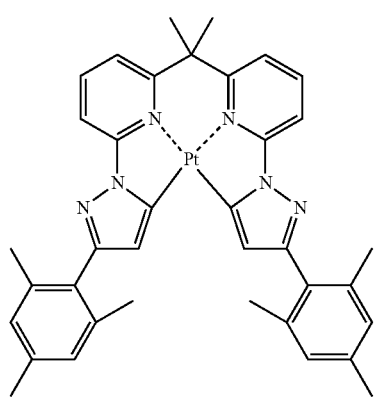
19
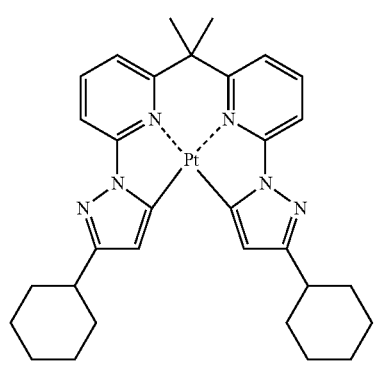
20
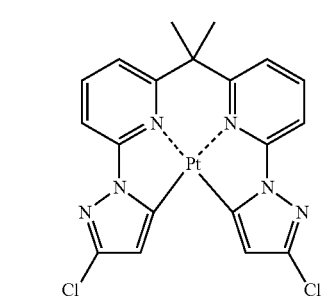
21
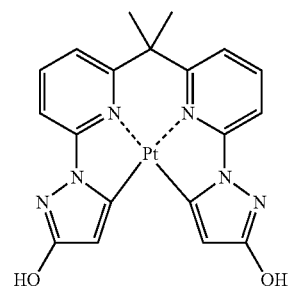
22
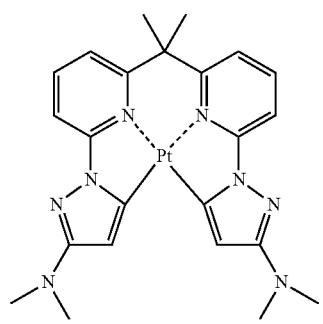
23
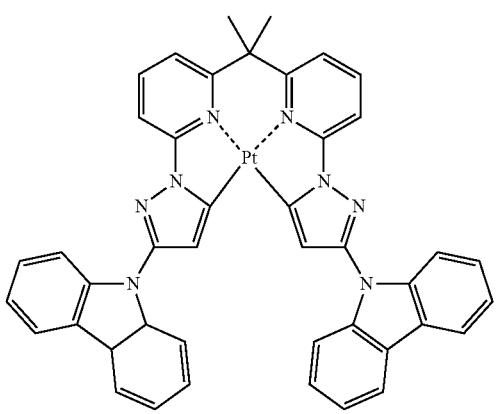
24
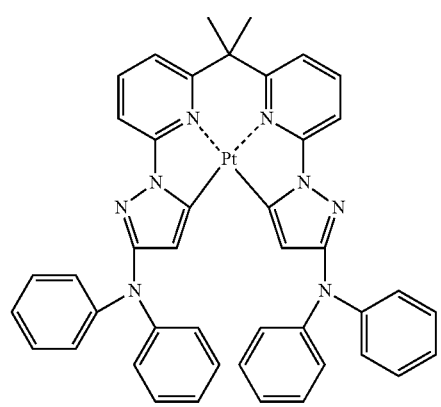

25
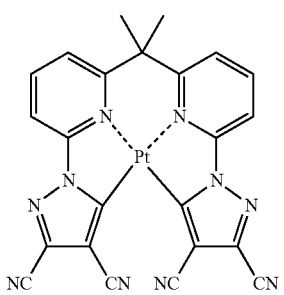
26
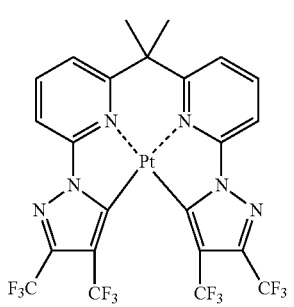
27
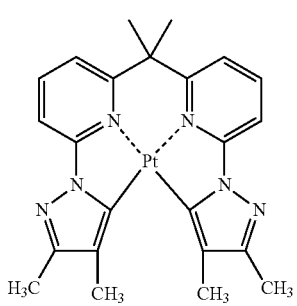
28
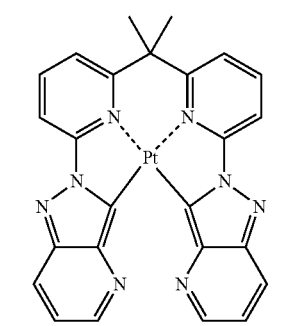
29
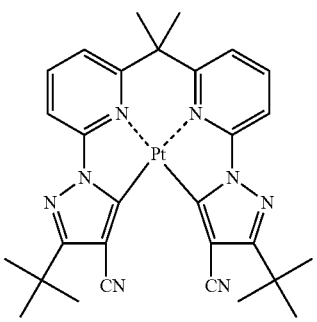
30
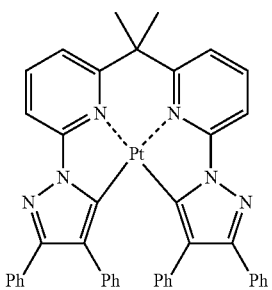
31
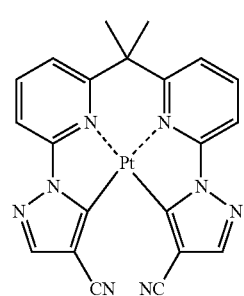
32
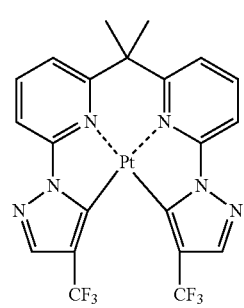
33
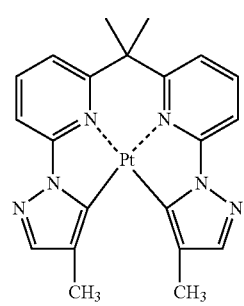
34
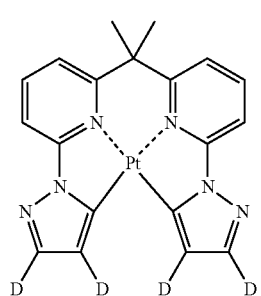

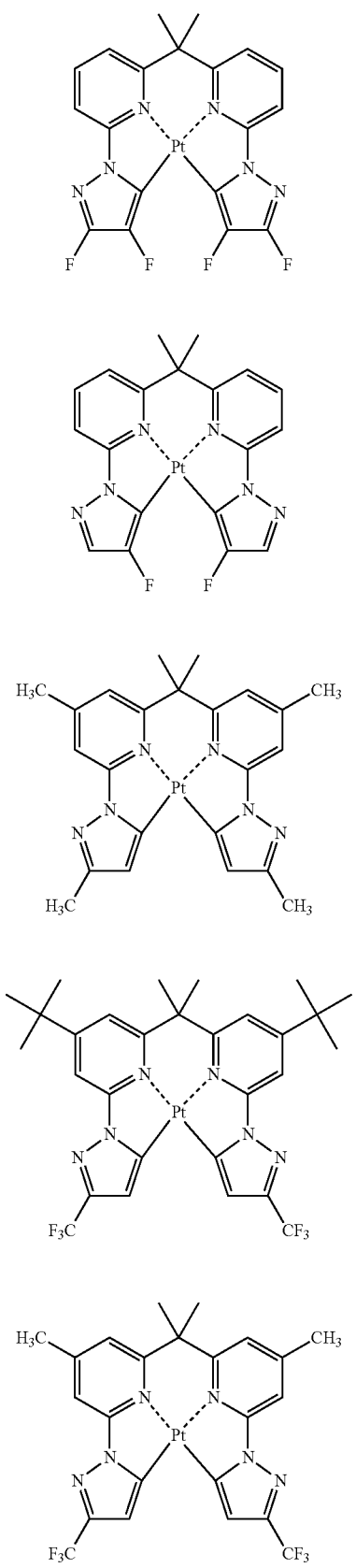

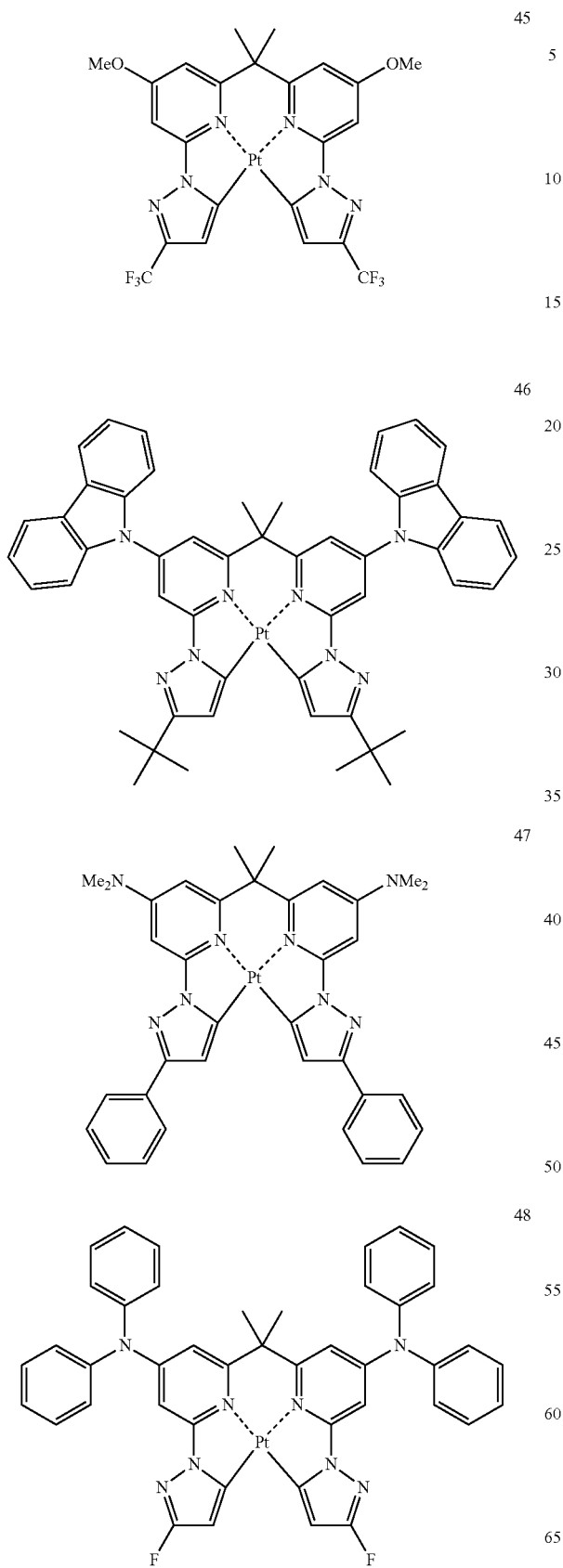
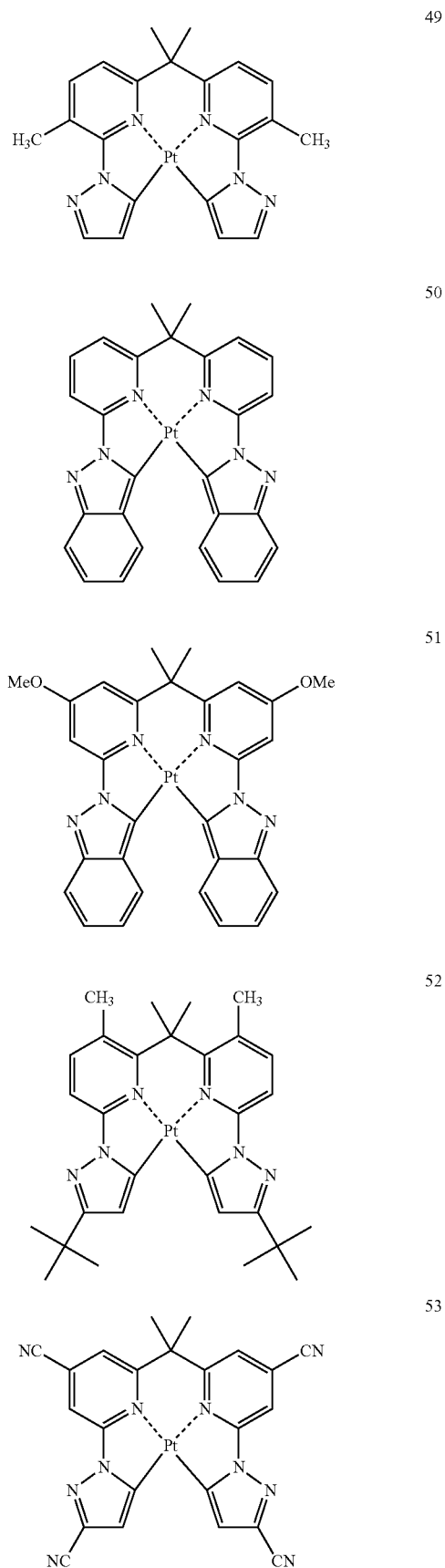

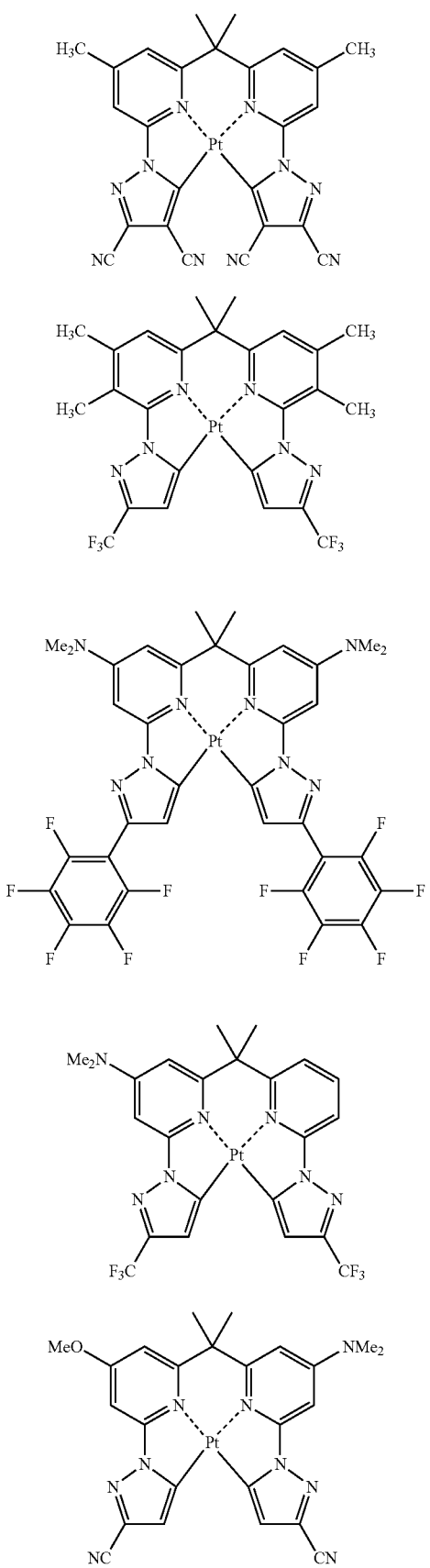
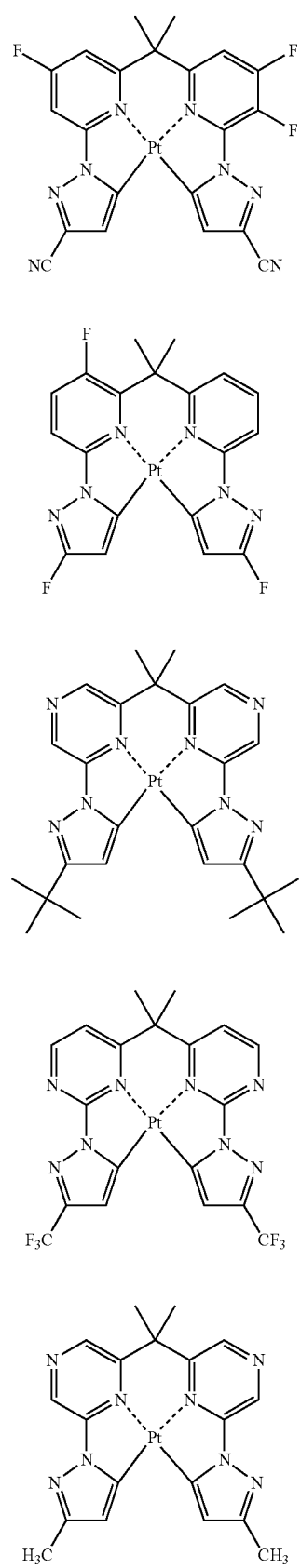

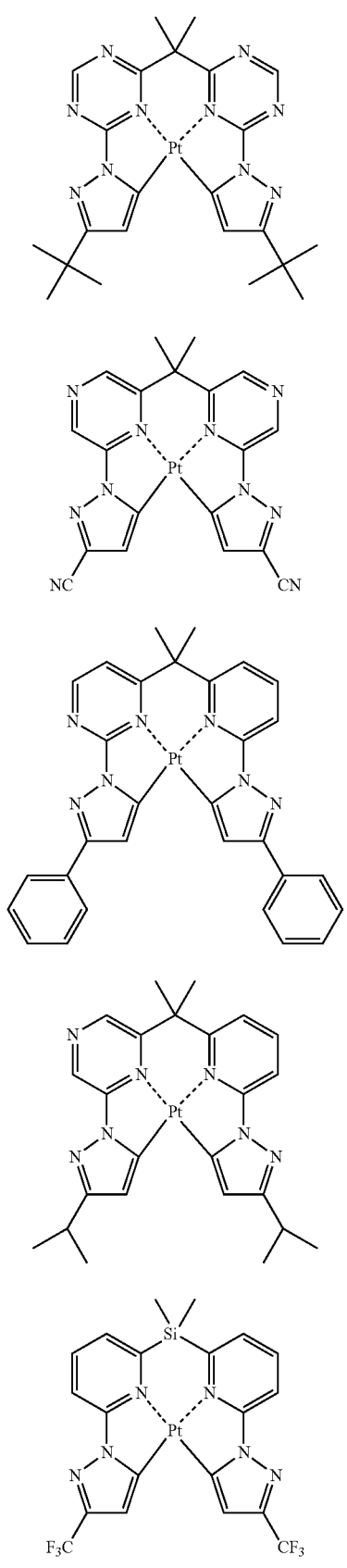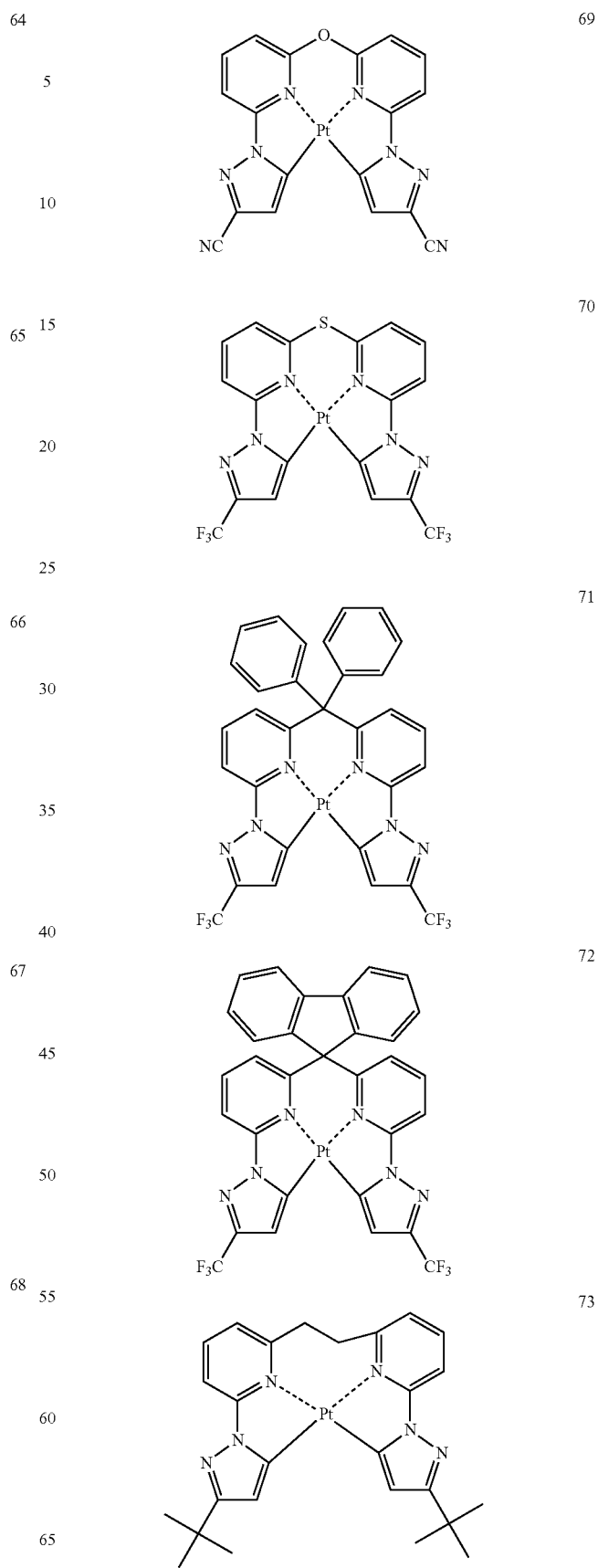

74
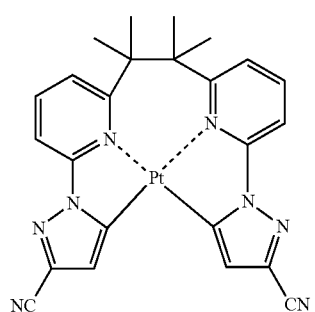
75
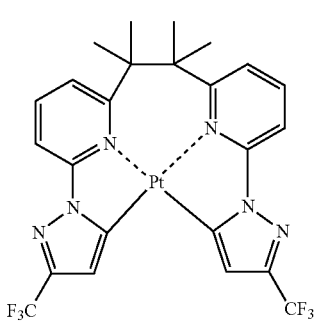
76
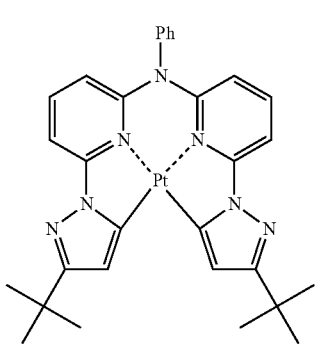
77
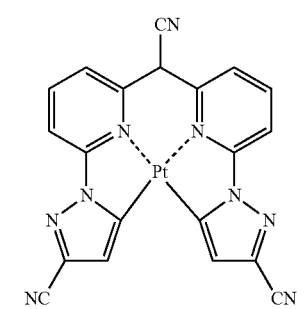
78
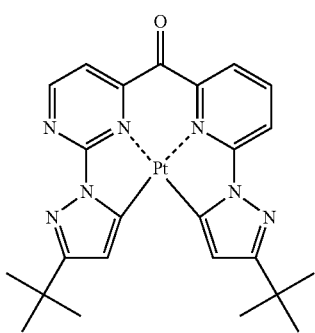
79
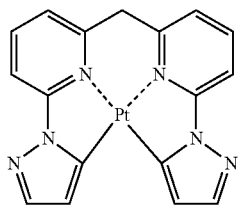
80
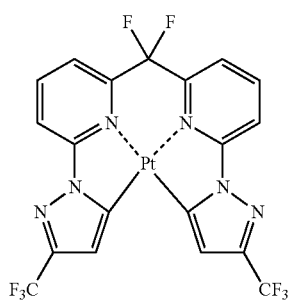
81
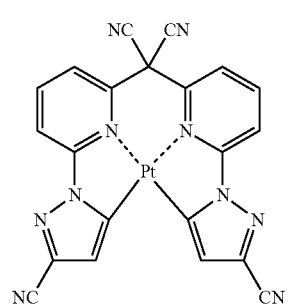
82
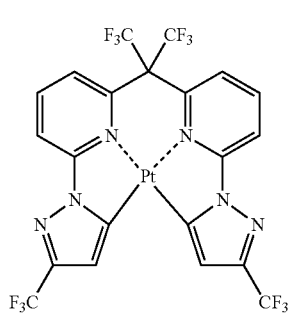
83
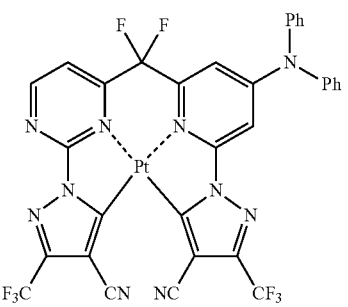

84 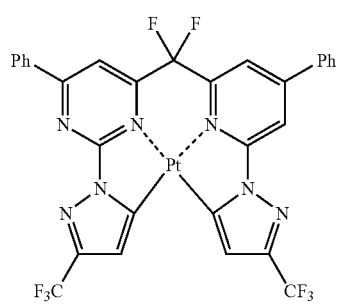
85 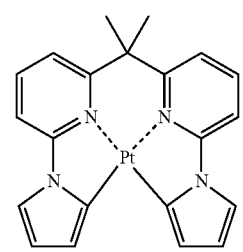
86 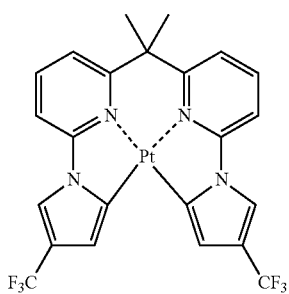
87 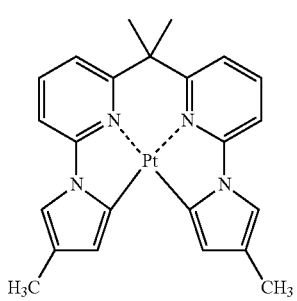
88 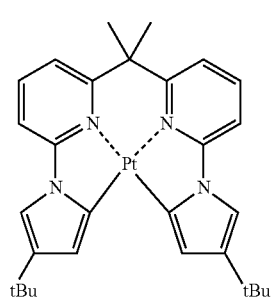
89 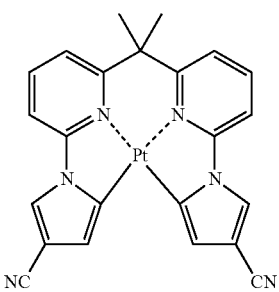
90 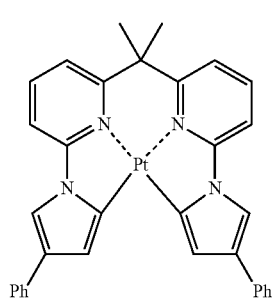
91 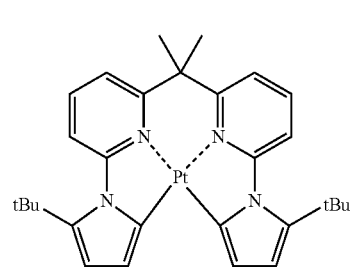
92 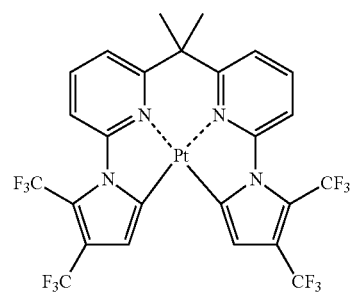
93 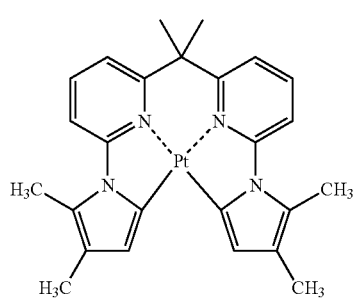

94 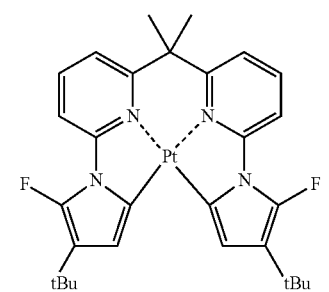
95 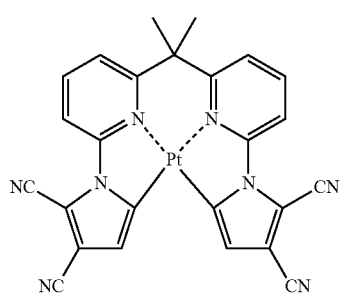
96 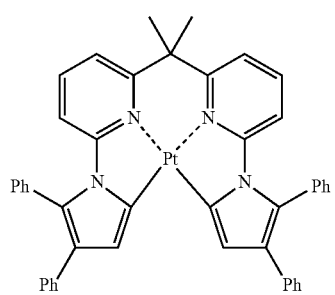
97 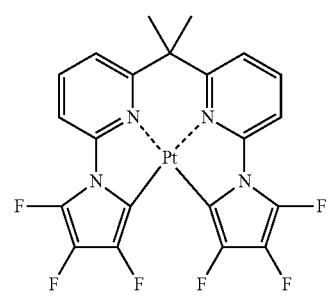
98 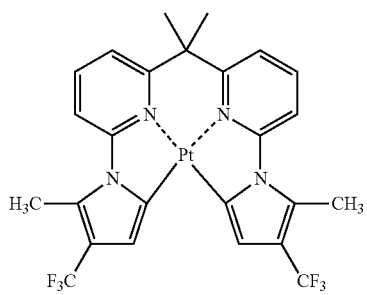
99 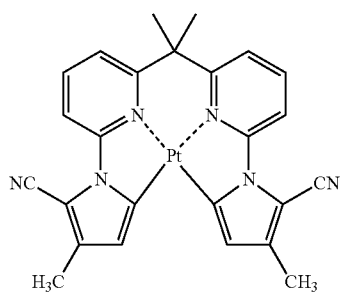
100 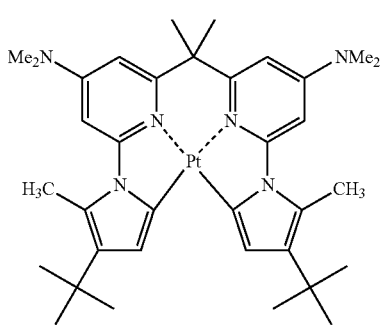
101 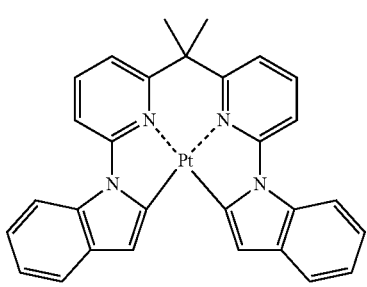
102 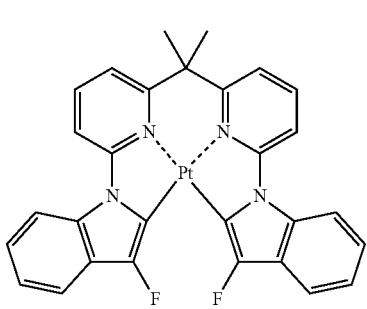
103 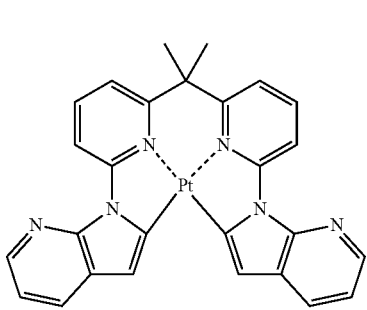

-continued
104 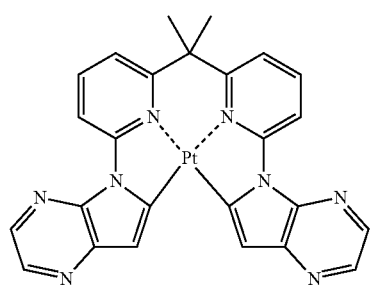
105 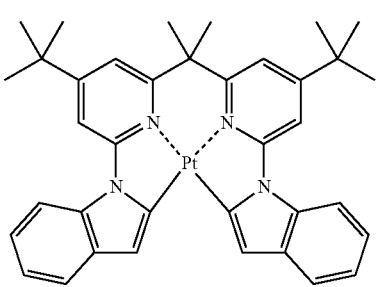
106 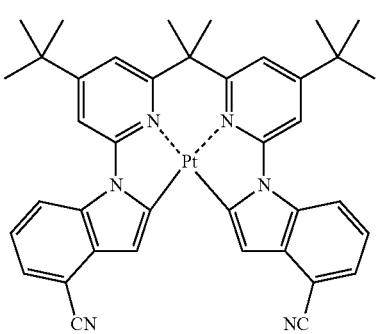
107 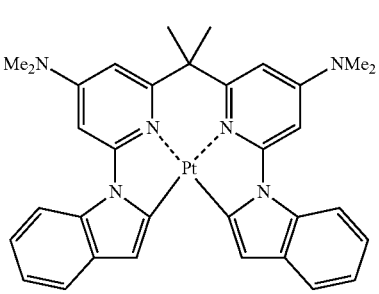
108 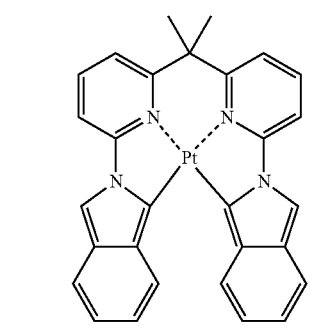
-continued
109 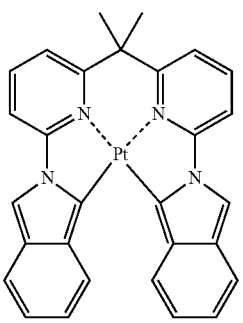
110 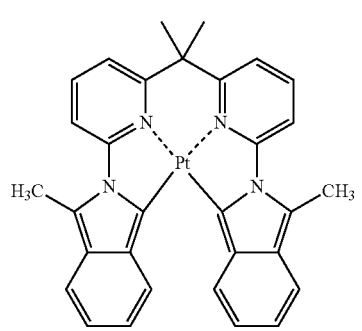
111 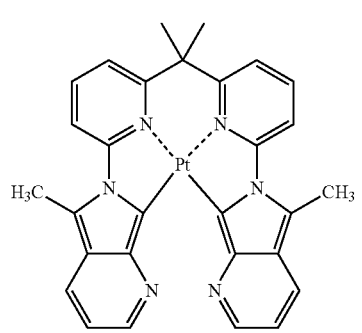
112 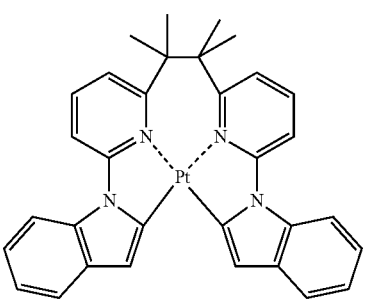
113 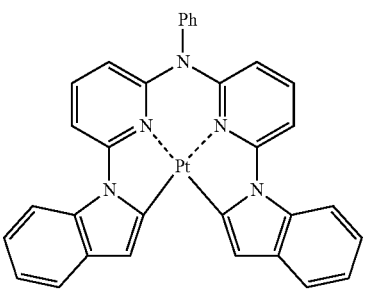

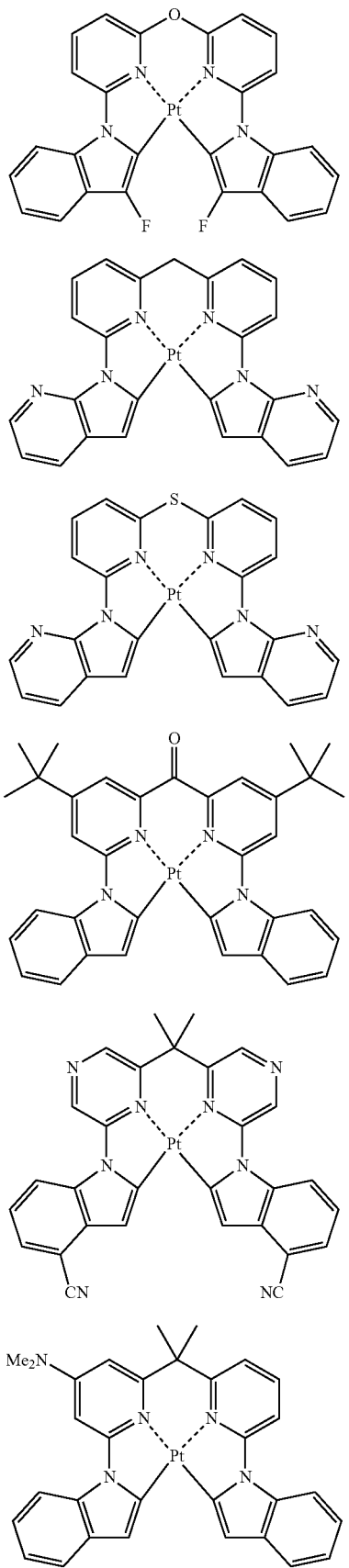

125
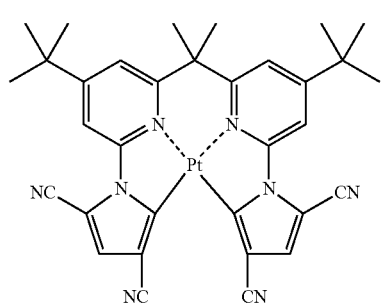
126
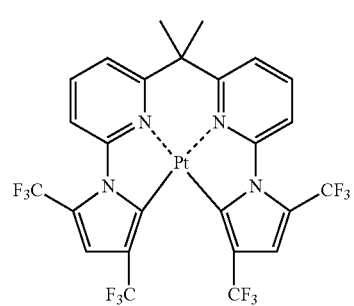
127
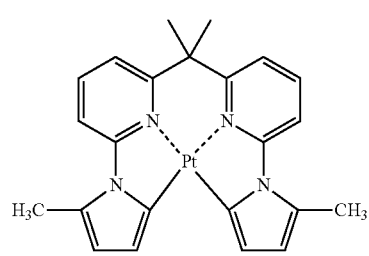
128
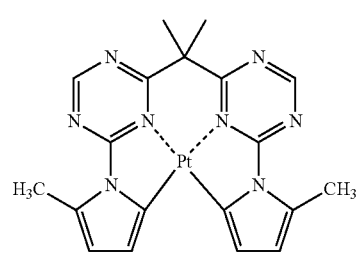
129
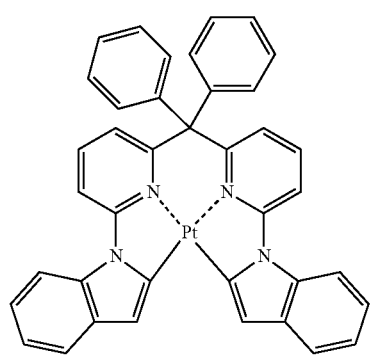
130
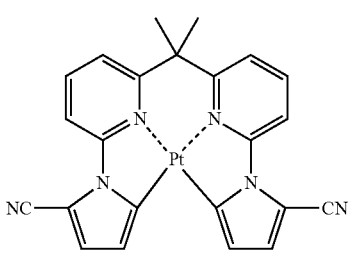
131
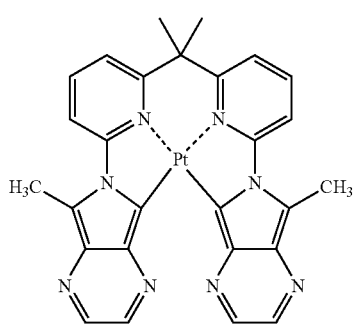
132
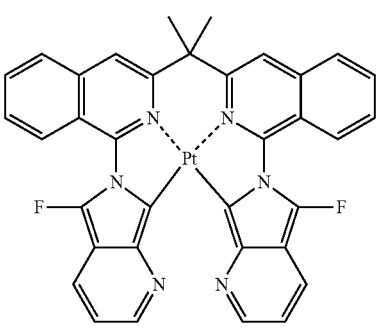
133
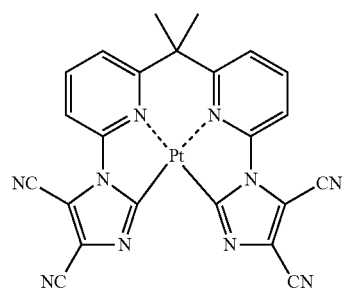
134
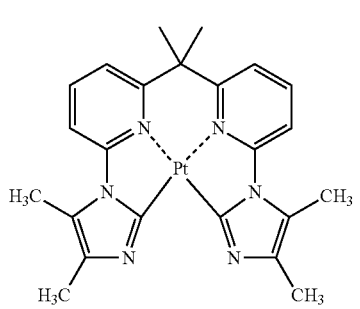

135
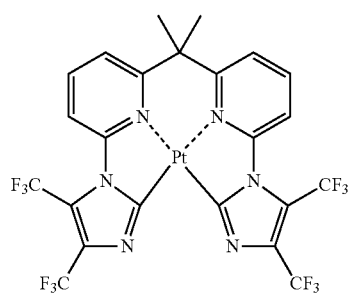
136
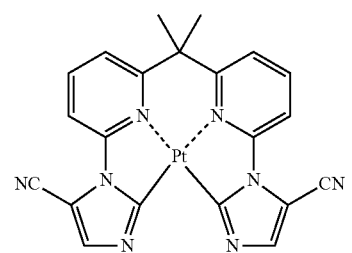
137
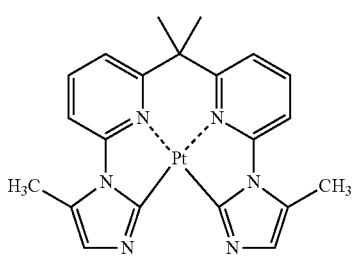
138
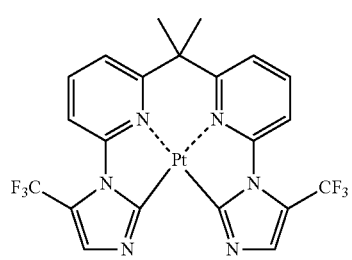
139
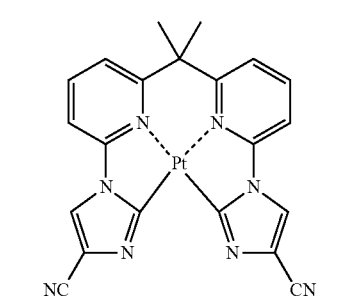
140
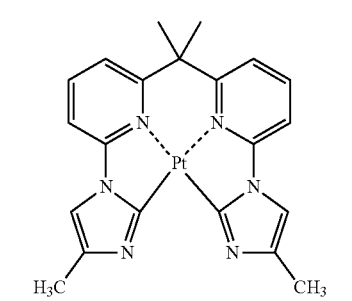
141
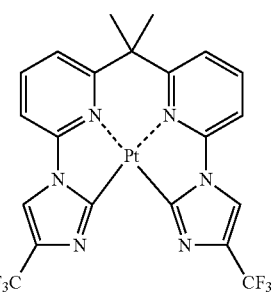
142
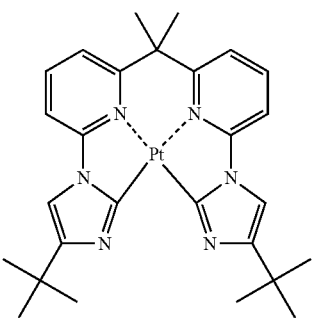
143
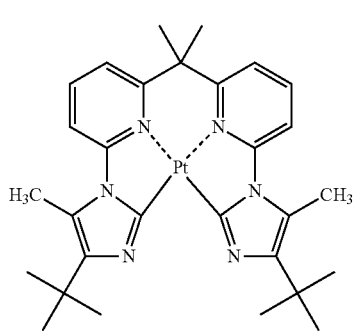
144
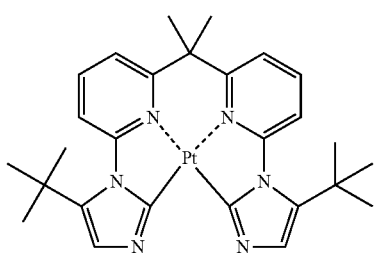
145
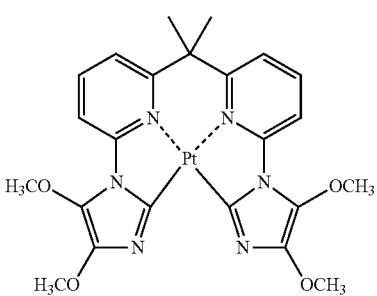

146
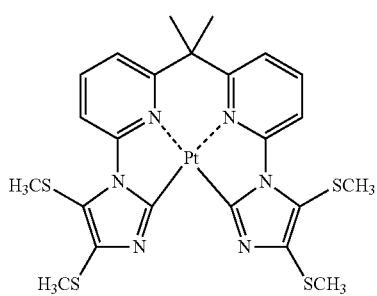
147
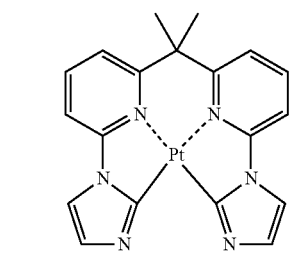
148
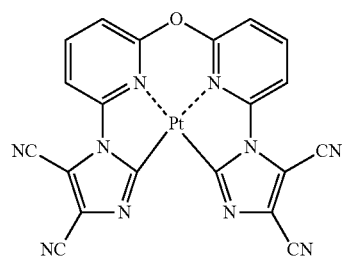
149
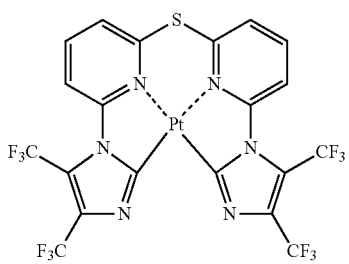
150
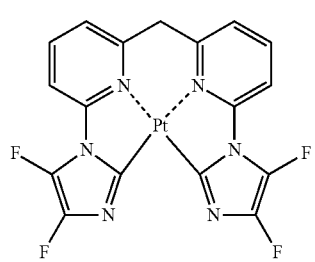
151
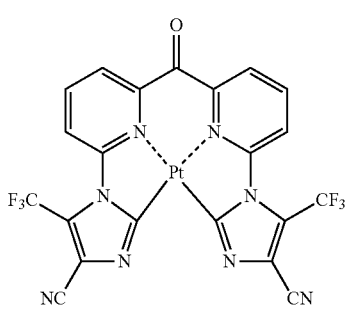
152
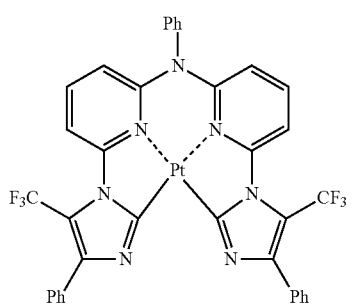
153
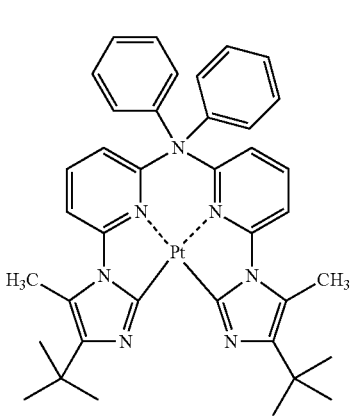
154
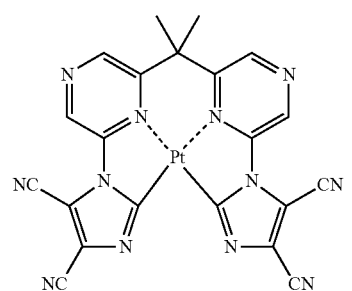
155
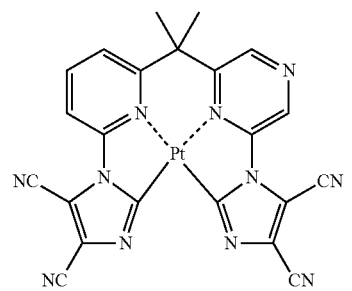
156
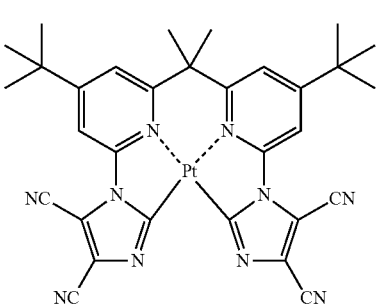

157
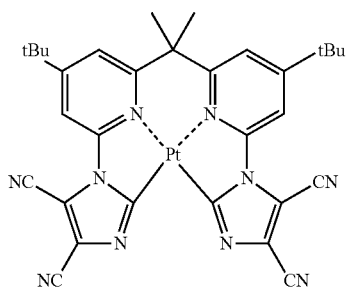
158
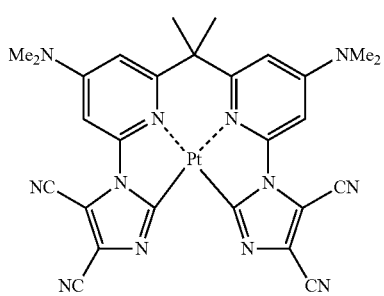
159
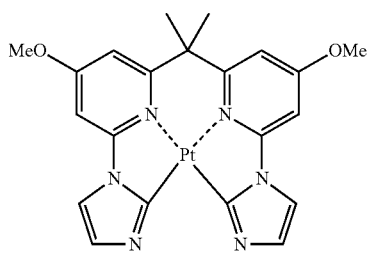
160
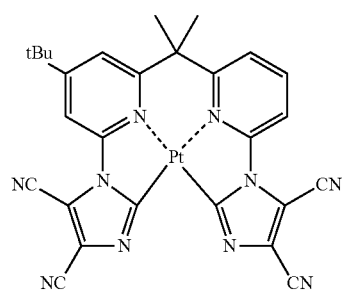
161
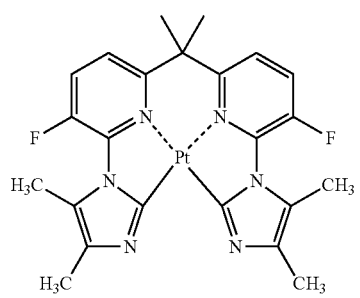
162
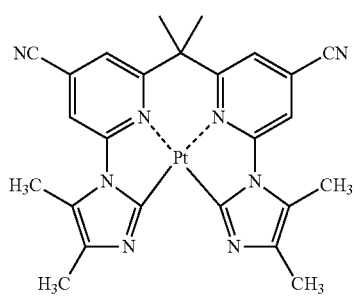
163
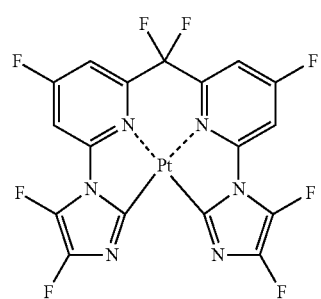
164
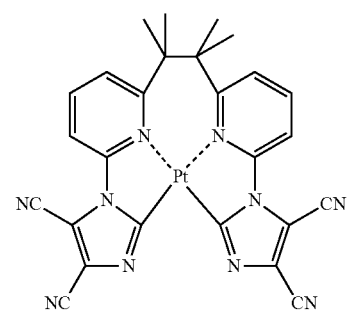
165
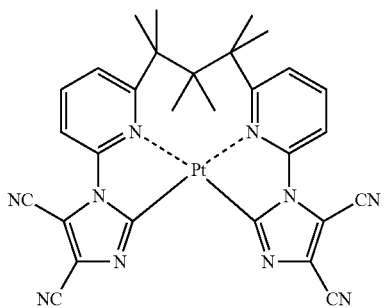
166
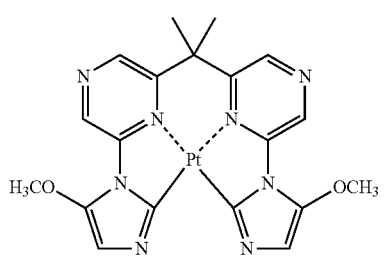

167 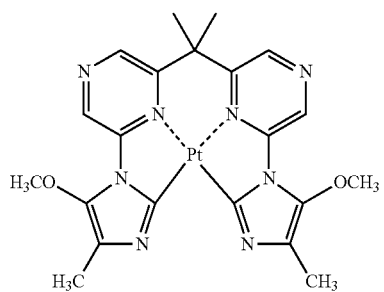
168 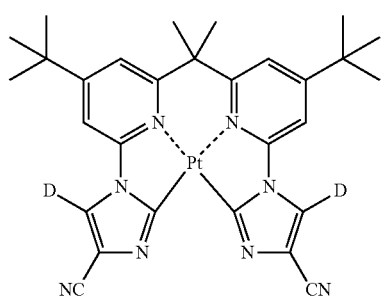
169 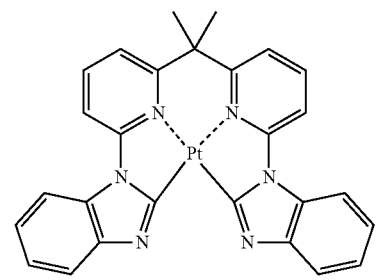
170 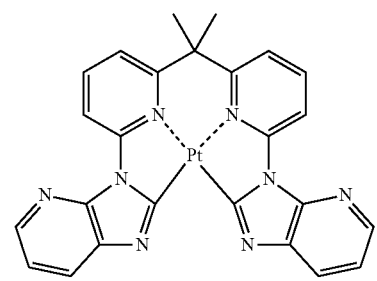
171 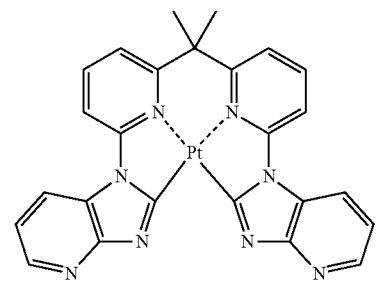
172 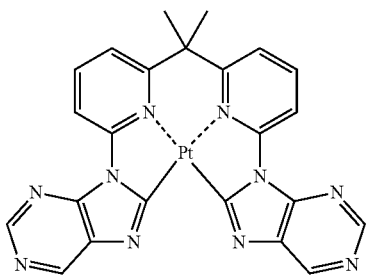
173 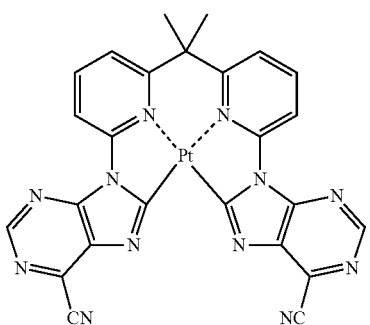
174 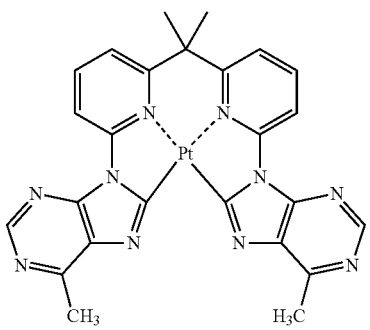
175 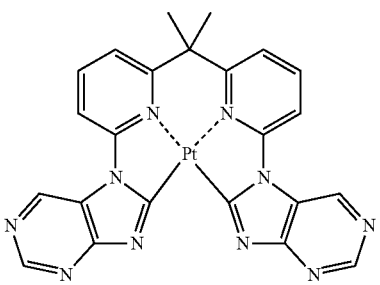
176 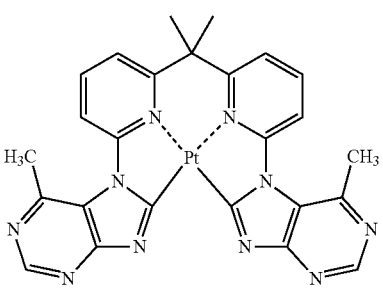

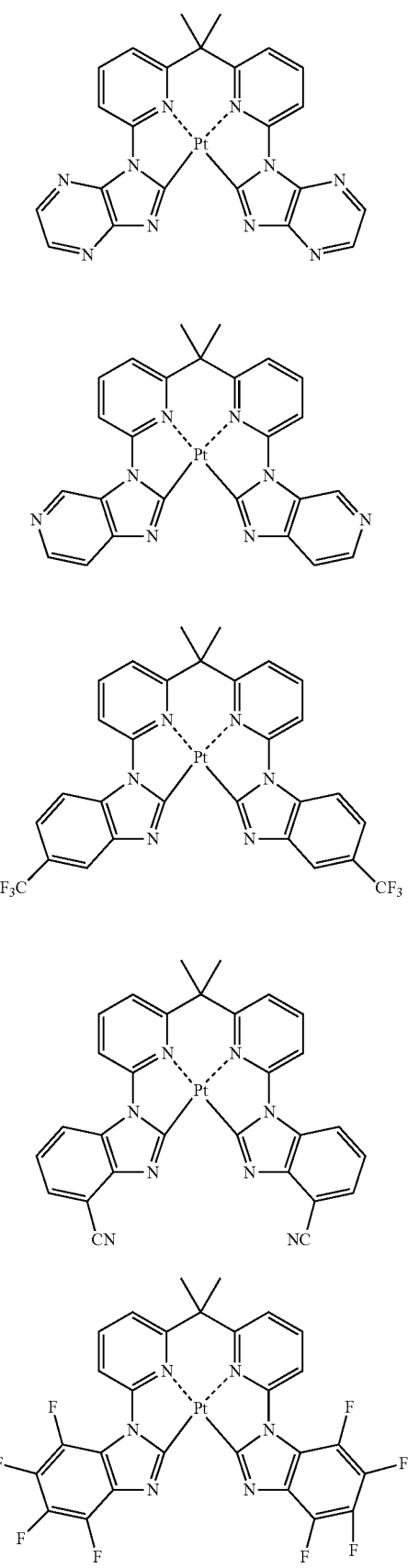
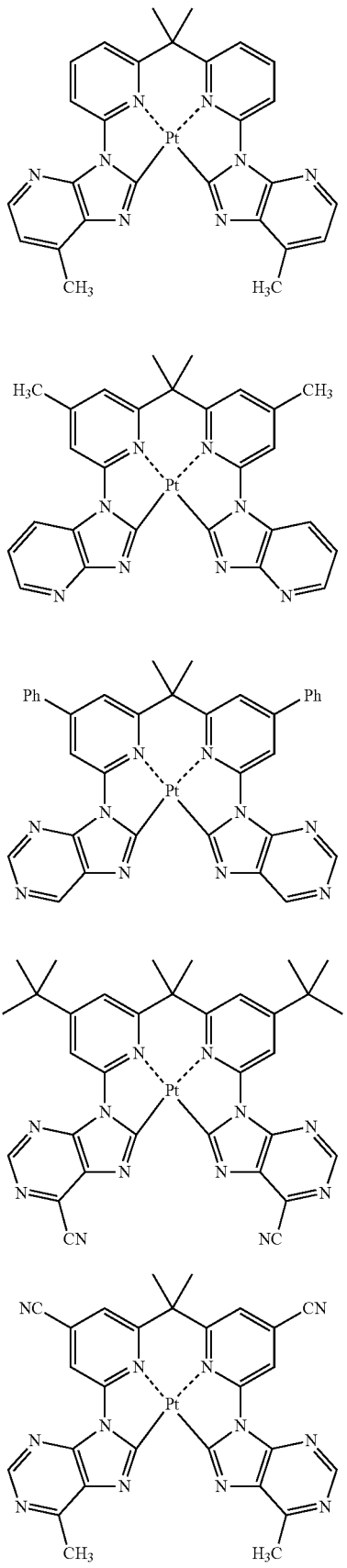

187 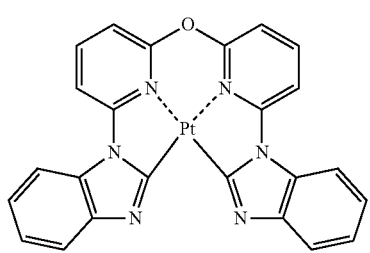
188 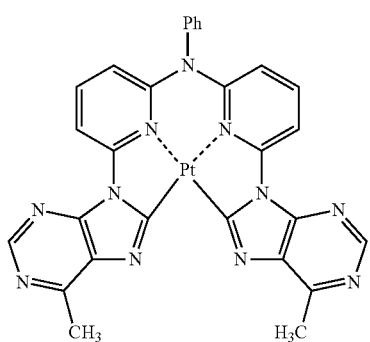
189 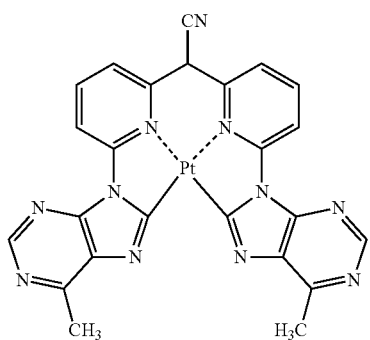
190 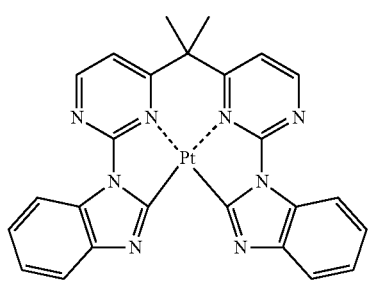
191 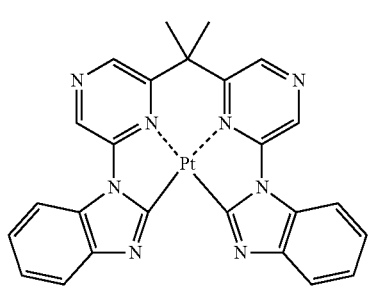
192 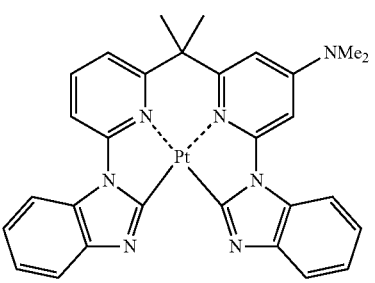
193 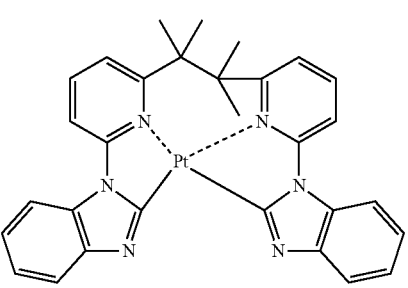
194 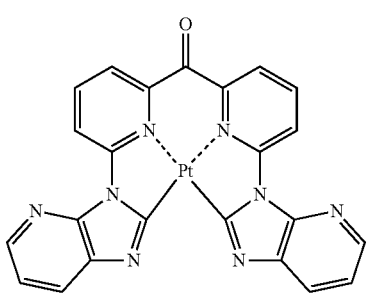
195 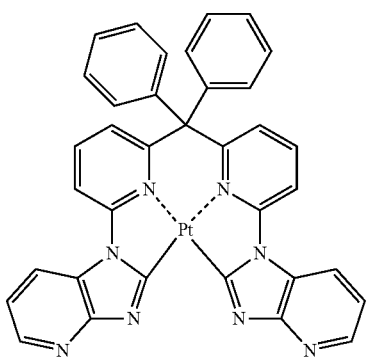
196 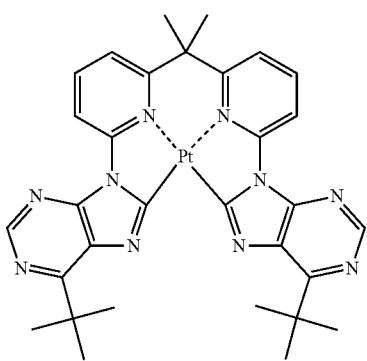

197
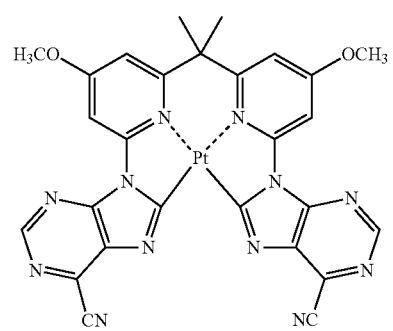
198
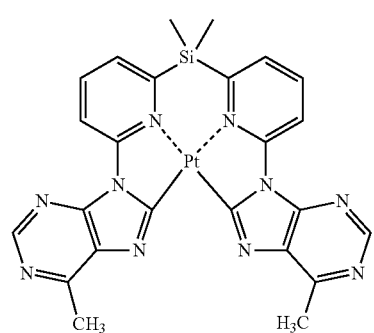
199
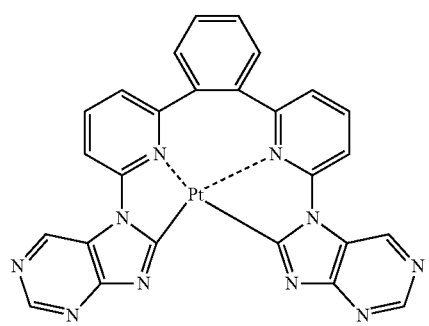
200
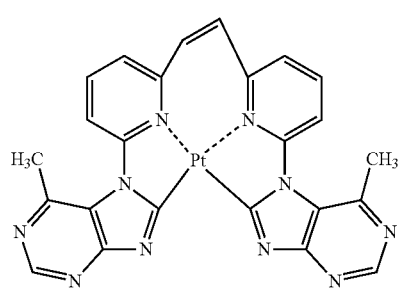
201
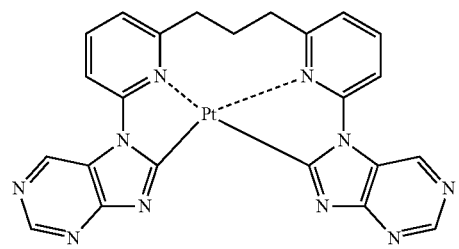
202
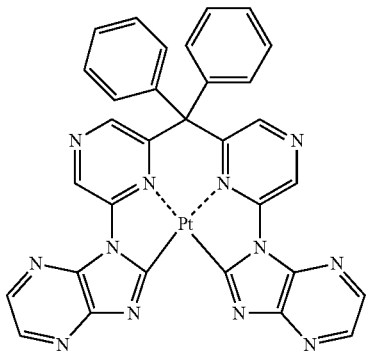
203
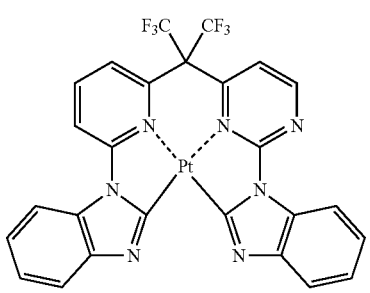
204
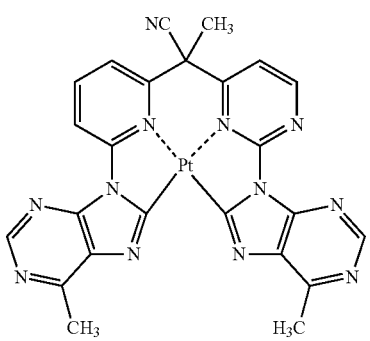
205
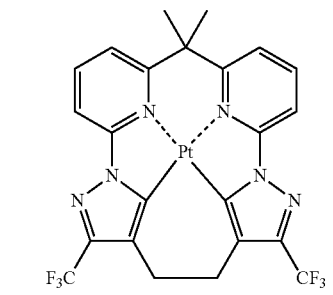
206
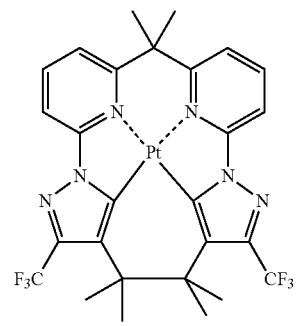

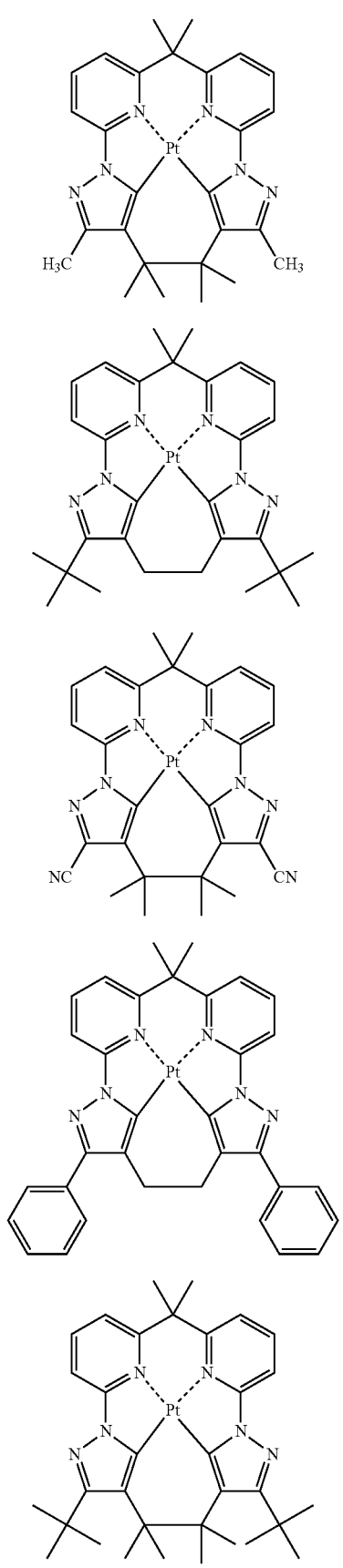
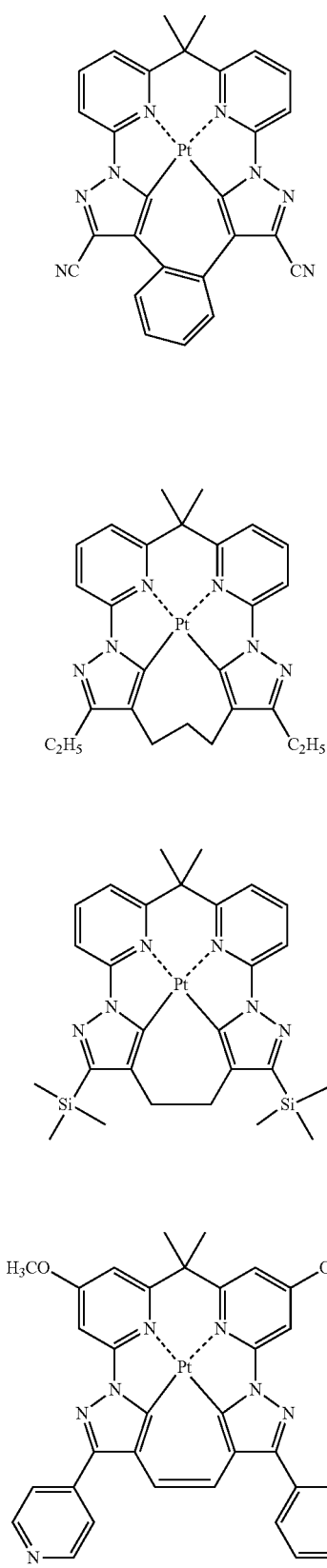

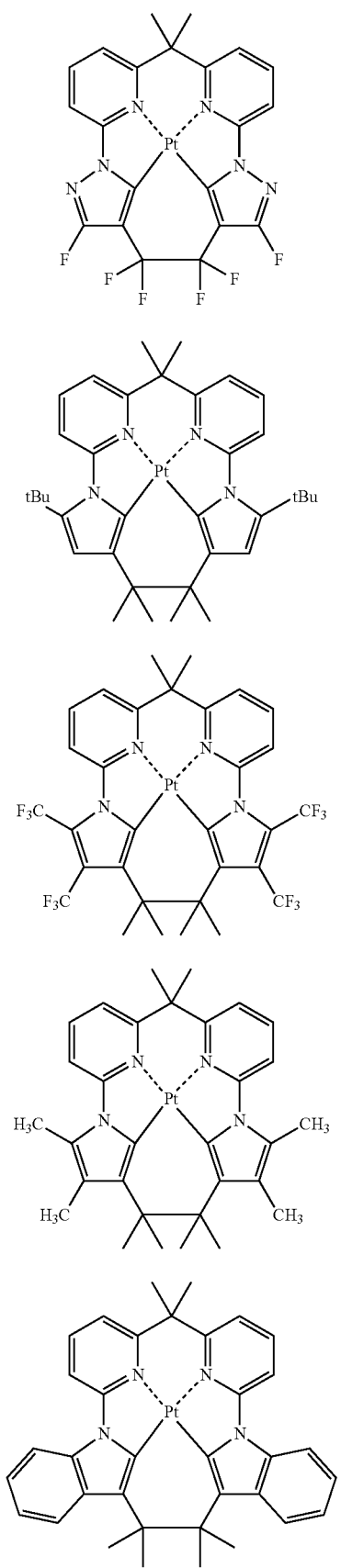
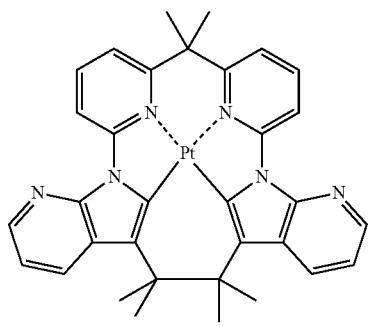
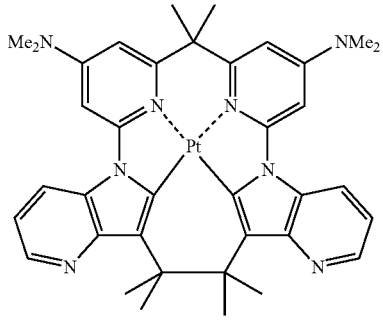
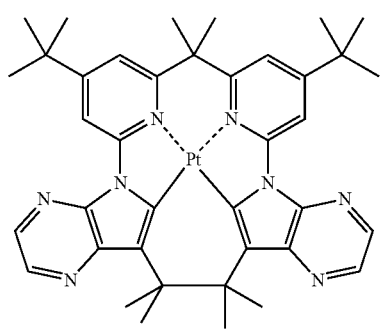
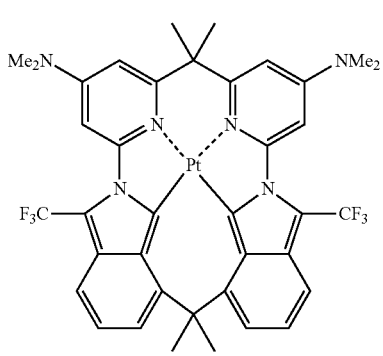
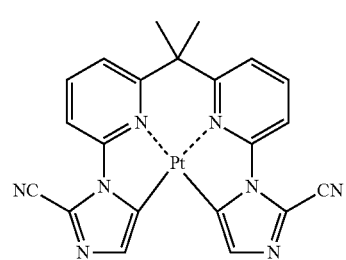

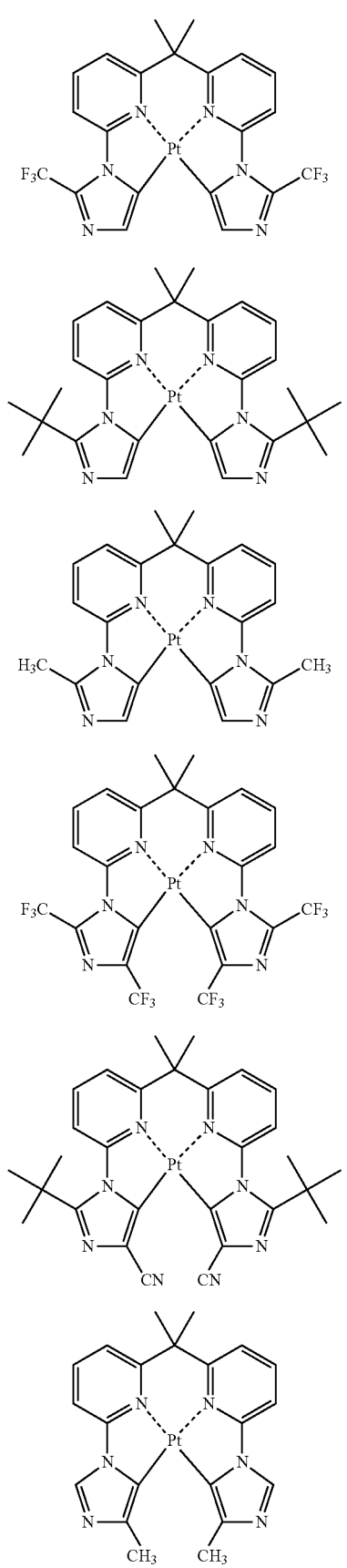
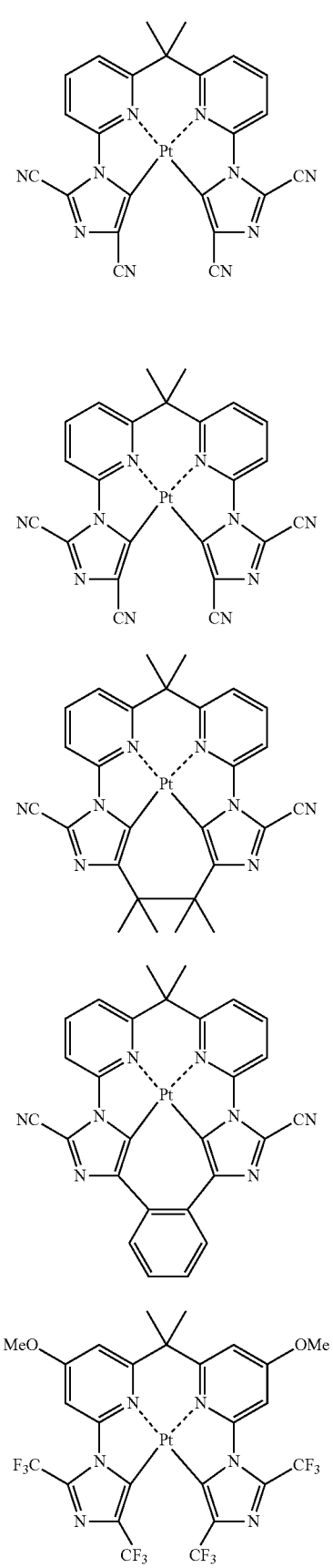

-continued
237 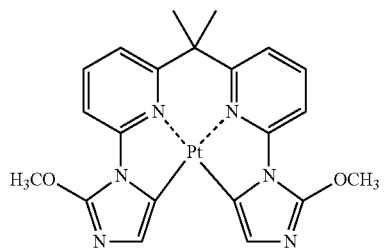
238 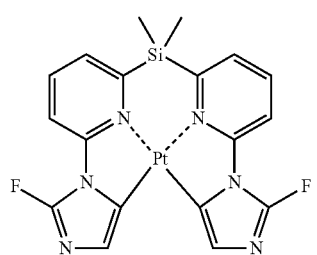
239 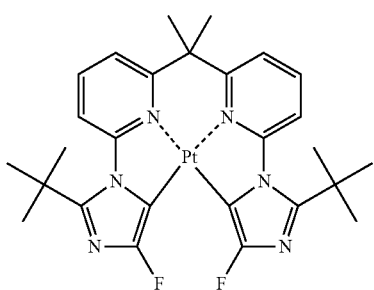
240 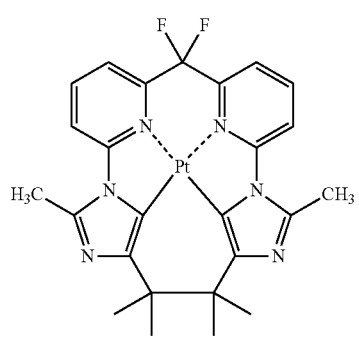
241 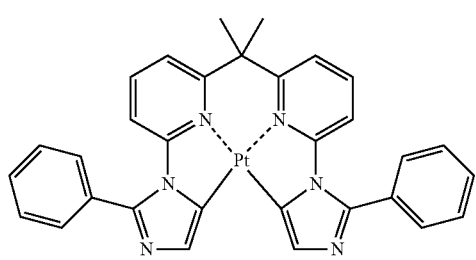
-continued
242 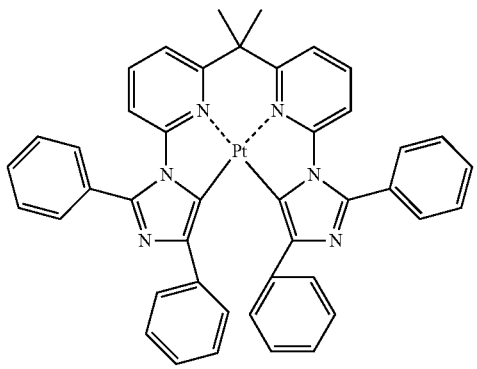
243 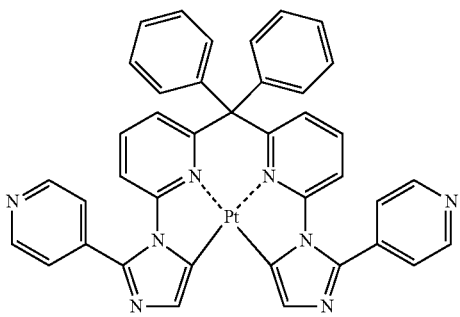
244 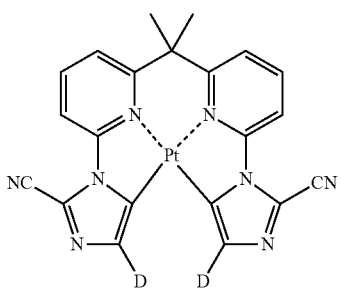
245 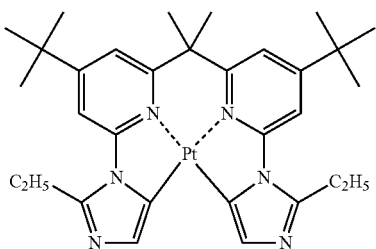
246 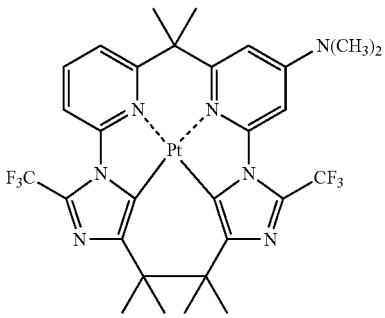

247 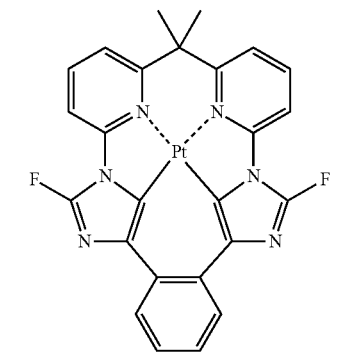
248 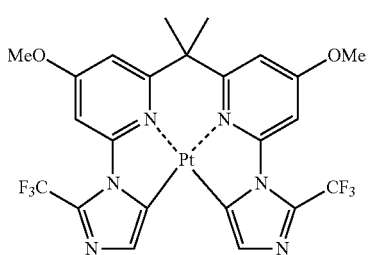
249 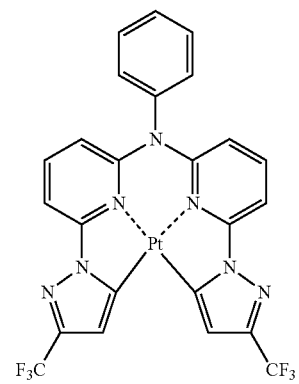
250 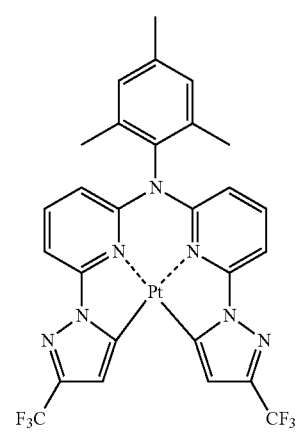
251 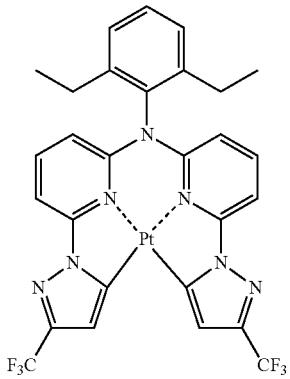
252 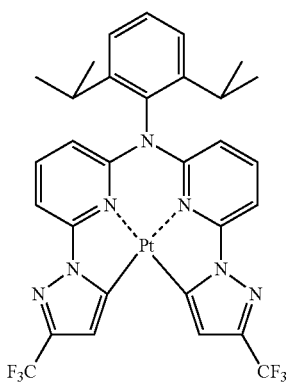
253 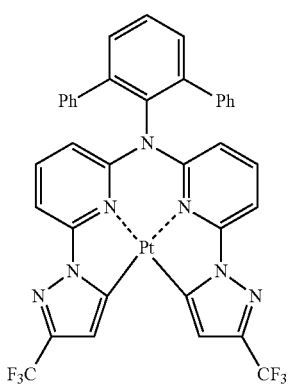
254 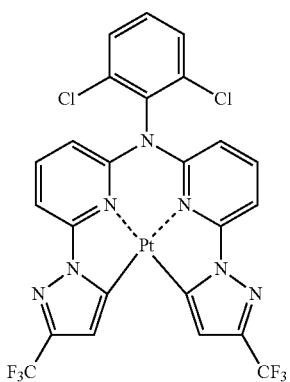

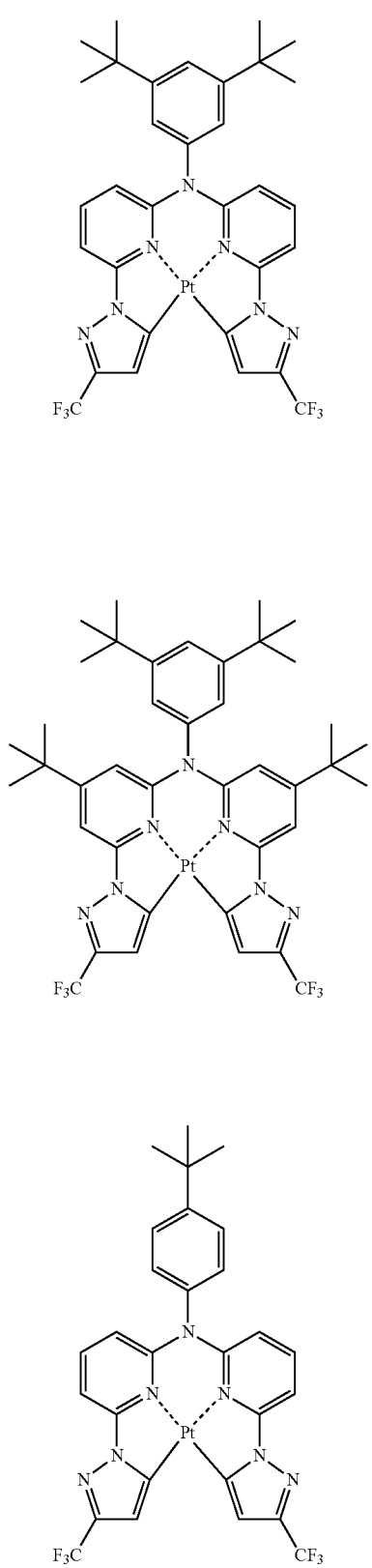
255
256
257
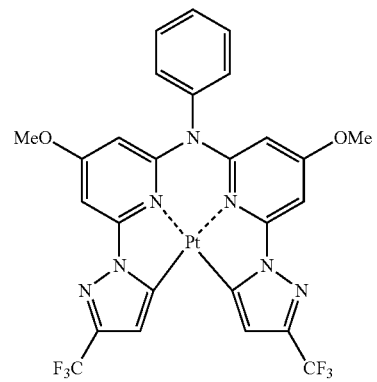
258
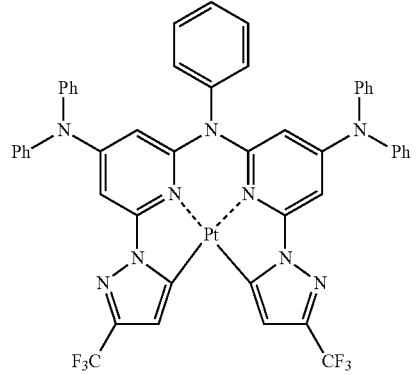
259
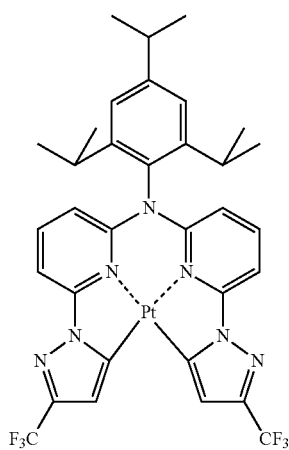
260
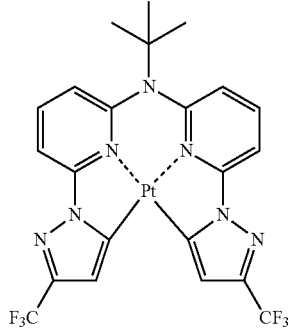
261

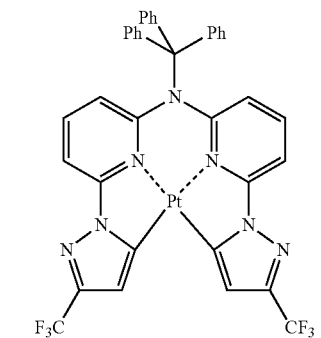
262
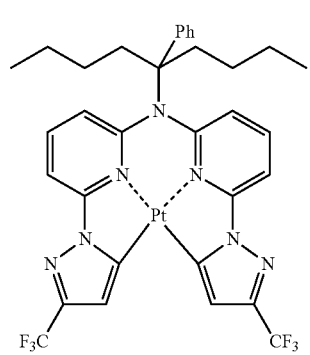
263
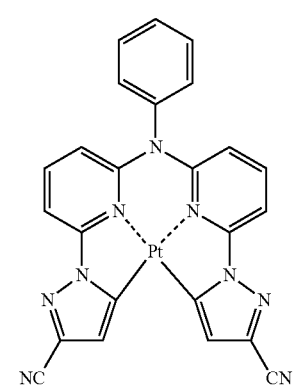
264
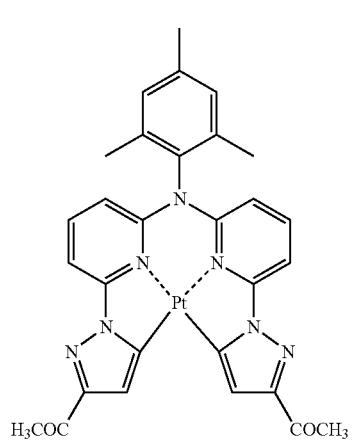
265
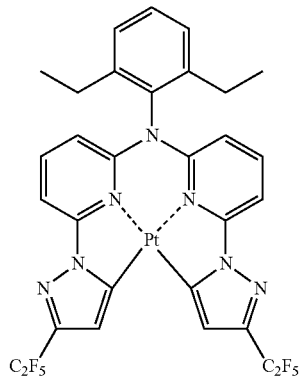
266
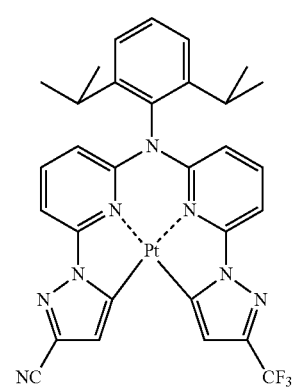
267
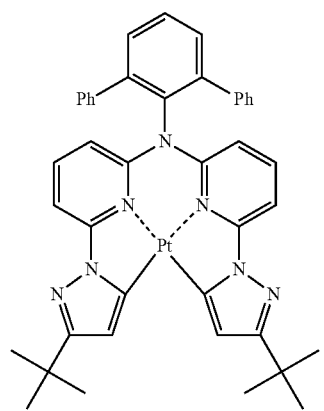
268
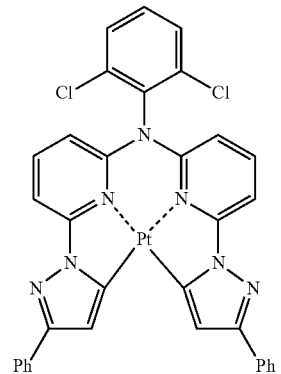
269

270
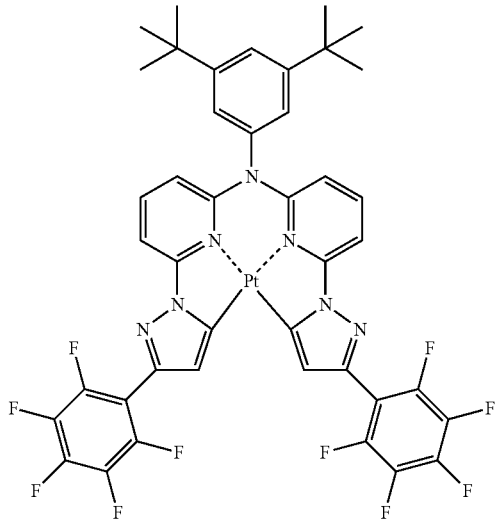
271
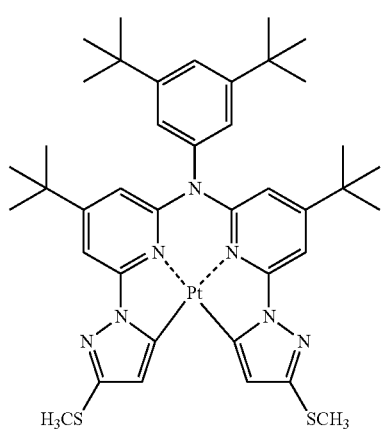
272
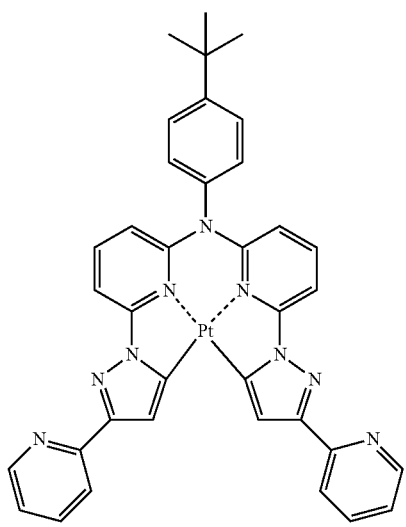
273
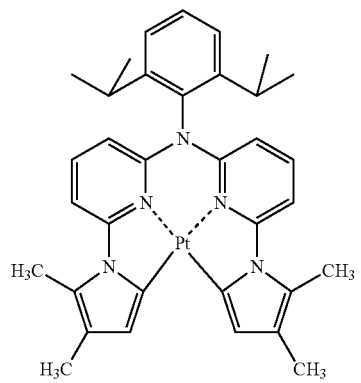
274
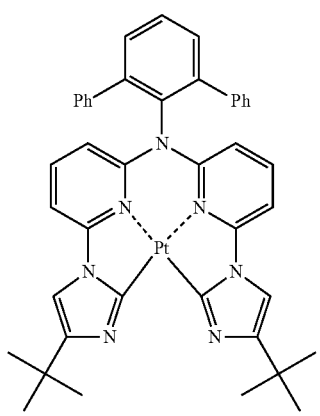
275
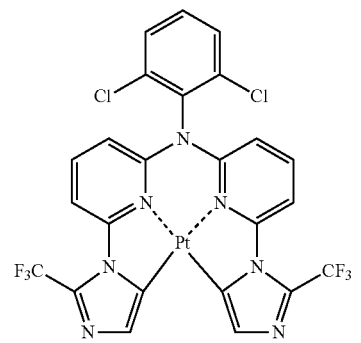
276
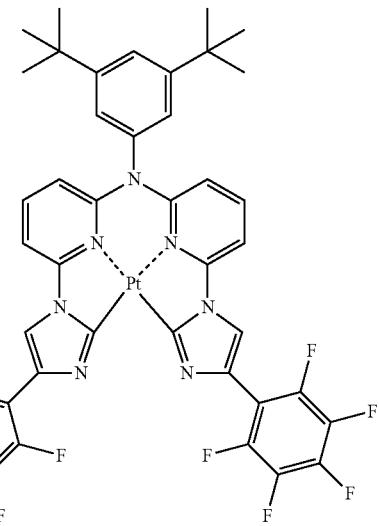

-continued

277

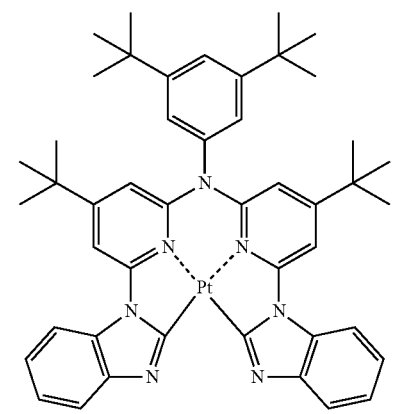

278

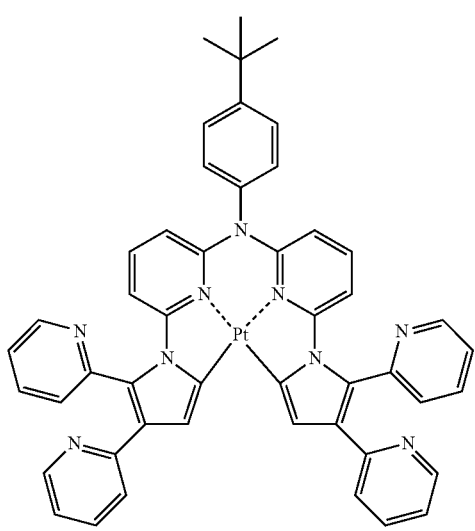

279

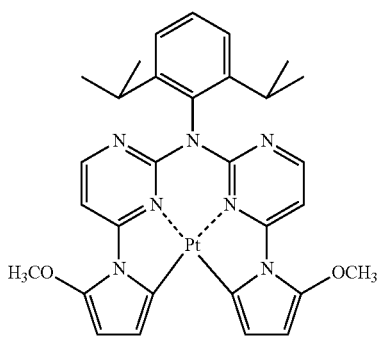

280

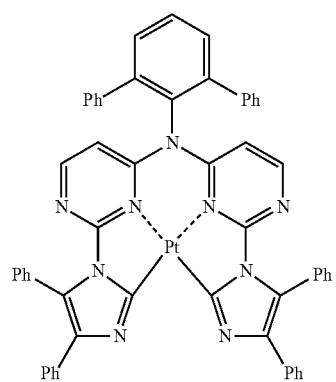

-continued

281

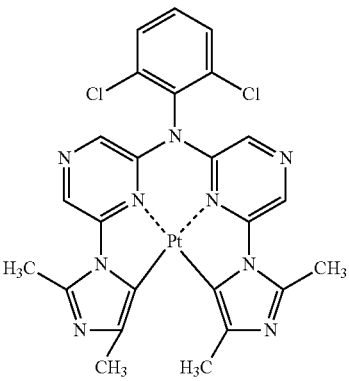

Each element constituting the device of the invention will be described in detail below.

<Substrate>

The substrate to be used in the invention is preferably a substrate which does not scatter or attenuate light emitted from the organic layer. Specific examples of materials for the substrate include inorganic materials such as yttrium-stabilized zirconia (YSZ) and glass, and organic materials such as polyesters (e.g., polyethylene terephthalate, polybutylene terephthalate and polyethylene naphthalate), polystyrene, polycarbonate, polyether sulfone, polyarylate, polyimide, polycycloolefin, norbornene resin and poly(chlorotrifluoroethylene).

In the case of using, for example, a glass plate as the substrate, alkali-free glass is preferably used in order to reduce the amount of ion dissolved out of the glass. In the case of using soda lime glass, it is preferred to use it after providing thereon a barrier coat of, for example, silica. With the organic materials, those which have an excellent heat resistance, dimensional stability, solvent resistance, electrically insulating properties and workability are preferred.

The substrate is not particularly limited as to its shape, structure and size, and they can properly be selected according to the use and purpose of the light-emitting element. In general, the shape of the substrate is preferably a plate. The structure of the substrate may be a single-layer structure or a layered structure, and may be formed by a single member or two or more members.

The substrate may be colorless or colored and transparent but, in view of preventing scattering or attenuating light emitted from the organic light-emitting layer, the substrate is preferably colorless and transparent.

A moisture permeation-preventing layer (gas barrier layer) may be formed on one or both surfaces of the substrate. The moisture permeation-preventing layer (gas barrier layer) is preferably made of an inorganic material such as silicon nitride or silicon oxide. The moisture permeation-preventing layer (gas barrier layer) can be formed by a high frequency sputtering method. In the case of using a thermoplastic substrate, a hard coat layer or an undercoat layer may further be provided as needed.

<Anode>

All that is required for the anode is usually to have the function of feeding holes as an electrode to the organic layer. The anode is not particularly limited as to its shape, structure and size, and can properly be selected from among known electrode materials according to the use and purpose of the light-emitting element. As has been described hereinbefore, the anode is usually provided as a transparent anode.

Examples of the materials for the anode include a metal, an alloy, a metal oxide, an electrically conductive compound and a mixture thereof. Specific examples of the anode material include electrically conductive metal oxides such as antimony- or fluorine-doped tin oxide (ATO or FTO), tin oxide, zinc oxide, indium oxide, indium tin oxide (ITO) and indium zirconium oxide (IZO), metals such as gold, silver, chromium and nickel, a mixture or layered product of the metal and the electrically conductive metal oxide, inorganic electrically conductive substance such as copper iodide and copper sulfide, organic electrically conductive materials such as polyaniline, polythiophene and polypyrrole, and a layered product thereof and ITO. Of these, electrically conductive metal oxides are preferred. In view of productivity, high electrical conductivity and transparency, ITO is particularly preferred.

The anode can be formed on the aforesaid substrate according to a method properly selected from among, for example, a wet method such as a printing method or a coating method, a physical method such as a vacuum deposition method, a sputtering method or an ion plating method and a chemical method such as a CVD method or a plasma CVD method in consideration of adaptability for the materials constituting the anode. For example, in the case of selecting ITO, formation of the anode can be performed according to a direct-current or high-frequency sputtering method, a vacuum deposition method or an ion plating method.

In the organic electroluminescent device of the invention, position of the anode is not particularly limited and can properly be selected according to the use and the purpose of the light-emitting element. However, the anode is preferably formed on the substrate. In this case, the anode may be provided all over, or part of, one surface of the substrate.

Additionally, patterning upon formation of the anode may be conducted by chemical etching according to photolithography, by physical etching using a laser, or by vacuum deposition or sputtering while superposing a mask, or by a lift-off method or a printing method.

The thickness of the anode can properly be selected according to the material constituting the anode and therefore cannot be described in a general manner, but is usually from about 10 nm to about 50 µm, preferably from 50 nm to 20 µm.

The resistance value of the anode is preferably $10^3 \Omega/\square$ or less, more preferably $10^2 \Omega/\square$ or less. In the case where the anode is transparent, it may be colorless and transparent, or colored and transparent. In order to emit light from the transparent anode side, the transmittance is preferably 60% or more, more preferably 70% or more.

Additionally, as to the transparent anode, detailed descriptions are given in *Tomei Denkyokumaku no Shintenkai (Developments of Transparent Electrode Films)* supervised by Yutaka Sawada and published by CMC Publishing Co., Ltd., 1999, which can be applied to the invention. In the case of using a plastic substrate having a low heat resistance, a transparent anode formed by filming at a temperature as low as 150° C. or lower using ITO or IZO is preferred.

<Cathode>

All that is required for the cathode is usually to have the function of injecting electrons to the organic layer as an electrode. The cathode is not particularly limited as to its shape, structure and size, and can properly be selected from among known electrode materials according to the use and purpose of the light-emitting element.

As materials for constituting the cathode, there are illustrated metals, alloys, metal oxides, electrically conductive compounds and mixtures thereof. Specific examples thereof include alkali metals (e.g., Li, Na, K and Cs), alkaline earth metals (e.g., Mg and Ca), gold, silver, lead, aluminum, sodium-potassium alloy, lithium-aluminum alloy, magnesium-silver alloy, and rare earth metals (e.g., indium and ytterbium). These may be used independently but, in view of obtaining both stability and electron-injecting properties, two or more of them can preferably be used in combination.

Of these, alkali metals and alkaline earth metals are preferred as cathode-constituting materials in view of electron-injecting properties, and materials containing aluminum as a major component are preferred in the point of excellent storage stability.

The phrase "the materials containing aluminum as a major component" means aluminum itself, an alloy or mixture of aluminum and from 0.01 to 10% by weight of an alkali metal or alkaline earth metal (e.g., lithium-aluminum alloy or magnesium-aluminum alloy).

Additionally, the materials for the cathode are described in detail in JP-A-2-15595 and JP-A-5-121172, and materials described therein can also be applied in the invention.

The method for forming the cathode is not particularly limited, and the cathode may be formed according to a known method. For example, the cathode can be formed according to a method properly selected from among, for example, a wet method such as a printing method or a coating method, a physical method such as a vacuum deposition method, a sputtering method or an ion plating method and a chemical method such as a CVD method or a plasma CVD method in consideration of adaptability for the materials constituting the cathode. For example, in the case of selecting a metal as a material for the cathode, formation of the cathode can be performed by employing one, two or more of them simultaneously or successively according to the sputtering method or the like.

Patterning upon formation of the cathode may be conducted by chemical etching according to photolithography, by physical etching using a laser, or by vacuum deposition or sputtering while superposing a mask, or by a lift-off method or a printing method.

In the invention, position of the cathode is not particularly limited and may be provided all over, or part of, the organic layer.

Also, a dielectric layer of from 0.1 to 5 nm in thickness comprising a fluoride or oxide of an alkali metal or alkaline earth metal may be inserted between the cathode and the organic layer. This dielectric layer may be taken as a kind of electron injecting layer. The dielectric layer may be formed by, for example, a vacuum deposition method, a sputtering method or an ion plating method.

The thickness of the cathode may properly be determined according to the material constituting the cathode and can not be described in a general manner, but is usually from about 10 nm to about 5 µm, more preferably from 50 nm to 1 µm.

Also, the cathode may be transparent or opaque. Additionally, the transparent cathode can be formed by forming a thin film of a material for the cathode and then forming thereon a layer of a transparent conductive material such as ITO or IZO.

<Organic Layer>

The organic layer in the invention will be described below. The device of the invention has at least one organic layer containing a light-emitting layer. As other organic layers than the organic light-emitting layer, there are illustrated, as has been described hereinbefore, a hole transporting layer, an electron transporting layer, a hole blocking layer, an electron blocking layer, a hole injecting layer and an electron injecting layer.

—Formation of Organic Layer—

In the organic electroluminescent device of the invention, each layer constituting the organic layer can preferably be formed by any of a dry film-forming method such as a vacuum deposition method or a sputtering method, a transferring method and a printing method.

—Light-Emitting Layer—

The light-emitting layer is a layer which, upon applying thereto an electric field, receives holes from the anode, the hole injecting layer or the hole transporting layer and receives electrons from the cathode, the electron injecting layer or the electron transporting layer and which functions to provide a place where the hole and the electron re-combine with each other to emit light.

The light-emitting layer in the invention may be constituted by the light-emitting material alone or may be constituted as a mixture layer of the host material and the light-emitting material. The light-emitting material may be a fluorescent light-emitting material or a phosphorescent light-emitting material. As dopants, one or more dopants may be used. The host material is preferably a charge transporting material. As the host materials, one or more host materials may be used. For example, there may be illustrated a structure wherein an electron transporting host material and a hole transporting host material are mixed with each other. Further, the light-emitting layer may contain a material which does not have charge transporting properties and does not emit light. As the light-emitting layer, a light-emitting layer containing the complex of the invention as a light-emitting material is preferred. More preferably, the light-emitting layer is constituted by at least one host material and the complex of the invention.

Also, the light-emitting layer may be a single layer or may be composed of two or more layers. The respective layers may emit lights of different colors.

Examples of the fluorescent light-emitting material to be used in the invention include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, ardazine derivatives, pyralizine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidine compounds, various complexes represented by complexes of 8-quinolinol derivatives and pyrromethene derivatives, polymer compounds such as polythiophene, polyphenylene and polyphenylenevinylene, and organic silane derivatives.

Also, as phosphorescent light-emitting materials to be used in the invention, there are illustrated, for example, transition metal atom- or lanthanide atom-containing complexes in addition to the complexes of the invention.

The transition metal atoms are not particularly limited, but are preferably ruthenium, rhodium, palladium, tungsten, rhenium, osmium, iridium and platinum, with rhenium, iridium and platinum being more preferred.

Examples of the lanthanide atoms include lanthanum, cerium, praseodymium, neodymium, samarium, europium, gadolinium, terbium, dysprosium, holmium, erbium, thulium, ytterbium and lutetium. Of these lanthanide atoms, neodymium, europium and gadolinium are preferred.

Examples of ligands for the complexes include those ligands which are described in *Comprehensive Coordination Chemistry* written by G. Wilkinson et al. and published by Pergamon Press in 1987; *Photochemistry and Photophysics of Coordination Compounds* written by H. Yersin and published by Springer-Verlag in 1987; and *Yuki Kinzoku Kagaku—Kiso to Oyo*—written by Akio Yamamoto and published by Shokabo in 1982.

Specific ligands are preferably a halogen atom (preferably a chlorine ligand), a nitrogen-containing hetero ring ligand (e.g., phenylpyridine, benzoquinoline, quninolinol, bipyridyl or phenanthroline), a diketone ligand (e.g., acetylacetone), a carboxylic acid ligand (e.g., acetic acid ligand), carbon monoxide ligand, isonitrile ligand and cyano ligand, with a nitrogen-containing hetero ring ligand being more preferred. The above-mentioned complexes may have one transition metal atom therein or may be so-called plural metal complexes having two or more transition metal atoms at the same time. Different metal atoms may be contained at the same time.

The phosphorescent light-emitting material is contained in the light-emitting layer in a content of preferably from 0.1 to 40% by weight, more preferably from 0.5 to 20% by weight.

As the host material to be contained in the light-emitting layer in the invention, there are illustrated for example, those described above, those which have a carbazole skeleton, those which have a diarylamine skeleton, those which have a pyridine skeleton, those which have a pyrazine skeleton, those which have a triazine skeleton and those which have an arylsilane skeleton, and those materials which are illustrated in the following items on the hole injecting layer, the hole transporting layer, the electron injecting layer and the electron transporting layer.

The thickness of the light-emitting layer is not particularly limited, but is preferably from 1 nm to 500 nm, more preferably from 5 nm to 200 nm, still more preferably from 10 nm to 100 nm.

—Hole Injecting Layer and Hole Transporting Layer—

The hole injecting layer and the hole transporting layer are layers having the function of receiving holes from the anode or the anode side and transporting them to the cathode side. The hole injecting layer and the hole transporting layer are specifically layers containing a carbazole derivative, a triazole derivative, an oxazole derivative, an oxadiazole derivative, an imidazole derivative, a polyarylalkane derivative, a pyrazoline derivative, a pyrazolone derivative, a phenylenediamfine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidine compound, a porphyrin compound, an organic silane derivative or carbon.

The thickness of the hole injecting layer or the hole transporting layer is preferably 500 nm or less from the viewpoint of reducing driving voltage.

The thickness of the hole transporting layer is preferably from 1 nm to 500 nm, more preferably from 5 nm to 200 nm, still more preferably from 10 nm to 100 nm. Also, the thickness of the hole injecting layer is preferably from 0.1 nm to 200 nm, more preferably from 0.5 nm to 100 nm, still more preferably from 1 nm to 100 nm.

The hole injecting layer and the hole transporting layer may have a single-layer structure comprising one or more of the above-mentioned materials, or may have a multi-layer structure composed of a plurality of layers comprising the same or different composition.

—Electron Injecting Layer and the Electron Transporting Layer—

The electron injecting layer and the electron transporting layer are layers having the function of receiving electrons from the cathode or the cathode side and transporting them to the anode side. Specifically, the electron injecting layer and the electron transporting layer are preferably layers containing a triazole derivative, an oxazole derivative, an oxadiazole derivative, an imidazole derivative, a fluorenone derivative, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, an aromatic ring (e.g., naphthalene or perylene) tetracarboxylic acid anhydride, a phthalocyanine derivative, a complex of 8-quinolinol derivative, metal phthalocyanine, various complexes represented by a complex containing benzoxazole or benzothiazole as a ligand or an organic silane derivative.

The thickness of the electron injecting layer or the electron transporting layer is preferably 50 nm or less from the viewpoint of reducing driving voltage.

The thickness of the electron transporting layer is preferably from 1 nm to 500 nm, more preferably from 5 nm to 200 nm, still more preferably from 10 nm to 100 nm. Also, the thickness of the electron injecting layer is preferably from 0.1 nm to 200 nm, more preferably from 0.2 nm to 100 nm, still more preferably from 0.5 nm to 50 nm.

The electron injecting layer and the electron transporting layer may have a single-layer structure comprising one or more of the above-mentioned materials, or may have a multi-layer structure composed of a plurality of layers comprising the same or different composition.

—Hole Blocking Layer—

The hole blocking layer is a layer having the function of preventing holes having been transported from the anode side from passing through to the cathode side. In the invention, the hole blocking layer may be provided as an organic layer adjacent to the light-emitting layer on its cathode side.

Examples of the organic compound constituting the hole blocking layer include an aluminum complex such as BAlq, a triazole derivative and a phenanthroline derivative such as BCP.

The thickness of the hole blocking layer is preferably from 1 nm to 500 nm, more preferably from 5 nm to 200 nm, still more preferably from 10 nm to 100 nm.

The hole blocking layer may have a single-layer structure comprising one or more of the above-mentioned materials, or may have a multi-layer structure composed of a plurality of layers comprising the same or different composition.

<Protective Layer>

In the invention, the whole organic EL element may be protected by a protective layer.

As materials to be incorporated in the protective layer, any of those materials may be used that prevent materials accelerating deterioration of the device, such as moisture and oxygen, from entering into the device.

Specific examples thereof include metals such as In, Sn, Pb, Au, Cu, Ag, Al, Ti and Ni, metal oxides such as MgO, SiO, $SiO_2$, $Al_2O_3$, GeO, NiO, CaO, BaO, $Fe_2O_3$, $Y_2O_3$ and $TiO_2$, metal nitrides such as $SiN_x$ and $SiN_xO_y$; metal fluorides such as $MgF_2$, LiF, $AlF_3$ and $CaF_2$, polyethylene, polypropylene, polymethyl methacrylate, polyimide, polyurea, polytetrafluoroethylene, polychlorotrifluoroethylene, polydichlorodifluoroethylene, a copolymer between chlorotrifluoroethylene and dichlorodifluoroethylene, a copolymer obtained by copolymerizing a monomer mixture containing tetrafluoroethylene and at least one comonomer, a fluorine-containing copolymer having a cyclic structure in the main chain of the copolymer, an water-absorbing substance having a water absorption of 1% or more and a moisture-proof substance having a water absorption of 0.1% or less.

The method for forming the protective layer is not particularly limited, and there may be applied, for example, a vacuum deposition method, a sputtering method, a reactive sputtering method, an MBE (molecular beam epitaxy) method, a cluster ion beam method, an ion plating method, a plasma polymerization method (high frequency-excited ion plating method), a plasma CVD method, a laser CVD method, a thermal CVD method, a gas source CVD method, a coating method, a printing method and a transfer method.

<Sealing>

The whole element of the invention may be sealed using a sealing container. A moisture-absorbing agent or an inert liquid may be encapsulated in the space between the sealing container and the device. The moisture-absorbing agent is not particularly limited, but is exemplified by barium oxide, sodium oxide, potassium oxide, calcium oxide, sodium sulfate, calcium sulfate, magnesium sulfate, phosphorus pentoxide, calcium chloride, magnesium chloride, copper chloride, cesium fluoride, calcium bromide, vanadium bromide, molecular sieve, zeolite and magnesium oxide. The inert liquid is not particularly limited, and is exemplified by paraffins, liquid paraffins, fluorine-containing solvents such as perfluoroalkane, perfluoramine and perfluoroether, chlorine-containing solvents and silicone oils.

The device of the invention can emit light when a direct current voltage (usually from 2 V to 15 V) (optionally containing an alternating component) or a direct current is applied across the anode and the cathode.

As to a method of driving the device of the invention, driving methods described in, for example, JP-A-2-148687, JP-A-6-301355, JP-A-5-29080, JP-A-7-134558, JP-A-8-234685, JP-A-8-241047, Japanese Patent No. 2,784,615, and U.S. Pat. Nos. 5,828,429 and 6,023,308 may be employed.

The device of the invention can appropriately be utilized for a display element, a display, a backlight, an electrophotographic system, a light source for illumination, a light source for recording, a light source for exposure, a light source for readout, a sign, a signboard, interior and optical communication.

The complex of the invention can be produced by, for example, the following scheme. A process for producing a compound represented by the formula (IIC) is specifically described below.

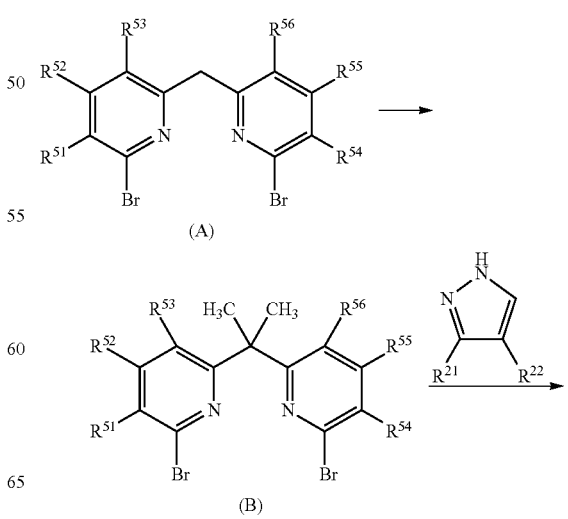

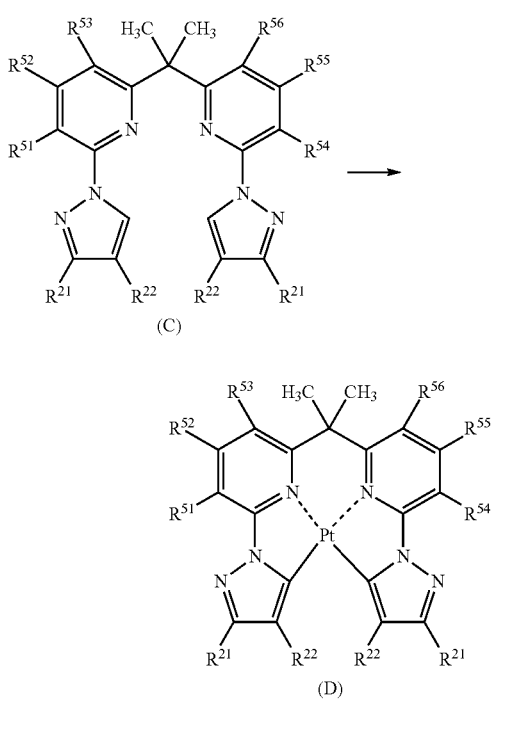

(C)

(D)

In the above formulae, $R^{21}$, $R^{22}$, $R^{51}$, $R^{52}$, $R^{53}$, $R^{54}$ and $R^{55}$ each independently represents a hydrogen atom or a substituent. The complex of the invention can be obtained according to the methods described in G. R. Newkome et al., *Journal of Organic Chemistry*, 53, 786 (1988), p. 789, left column, line 53 to right column, line 7, p. 790, left column, line 18 to line 38, p. 790, right column, line 19 to line 30, and a combination thereof. A dimethyl-substituted derivative (B) can be obtained in a yield of from 70% to 99% by using a compound (A) as a starting material, adding to a solution of the compound (A) in N,N-dimethylformamide a base such as lithium diisopropylamide, potassium t-butoxide or sodium hydride in an amount of 1 to 1.2 equivalents, conducting reaction at 0° C. to room temperature for 30 minutes, adding thereto 1.5 to 4 equivalents of methyl iodide, conducting reaction at room temperature for about 30 minutes to monomethylate, and then again reacting with 1 to 1.2 equivalents of the base and an excess amount of methyl iodide under the same condition.

The step of obtaining the compound (C) from the compound (B) can be conducted according to the method described in H. Lexy et al., *Chemische Berichte*, 113, 2749 (1980), p. 2752, lines 26 to 35 to thereby synthesize the compound (C).

The step of obtaining the compound (D) of the invention from the compound (C) can be conducted by dissolving the compound (C) and 1 to 1.5 equivalents of platinous chloride in benzonitrile, heating to 130° C. to a reflux temperature (boiling point of benzonitrile: 191° C.) for 30 minutes to 4 hours under stirring. The compound (D) can be purified by recrystallization using chloroform or ethyl acetate, by silica gel column chromatography or by sublimation purification.

A compound (H) of the invention can be produced by, for example, the following scheme.

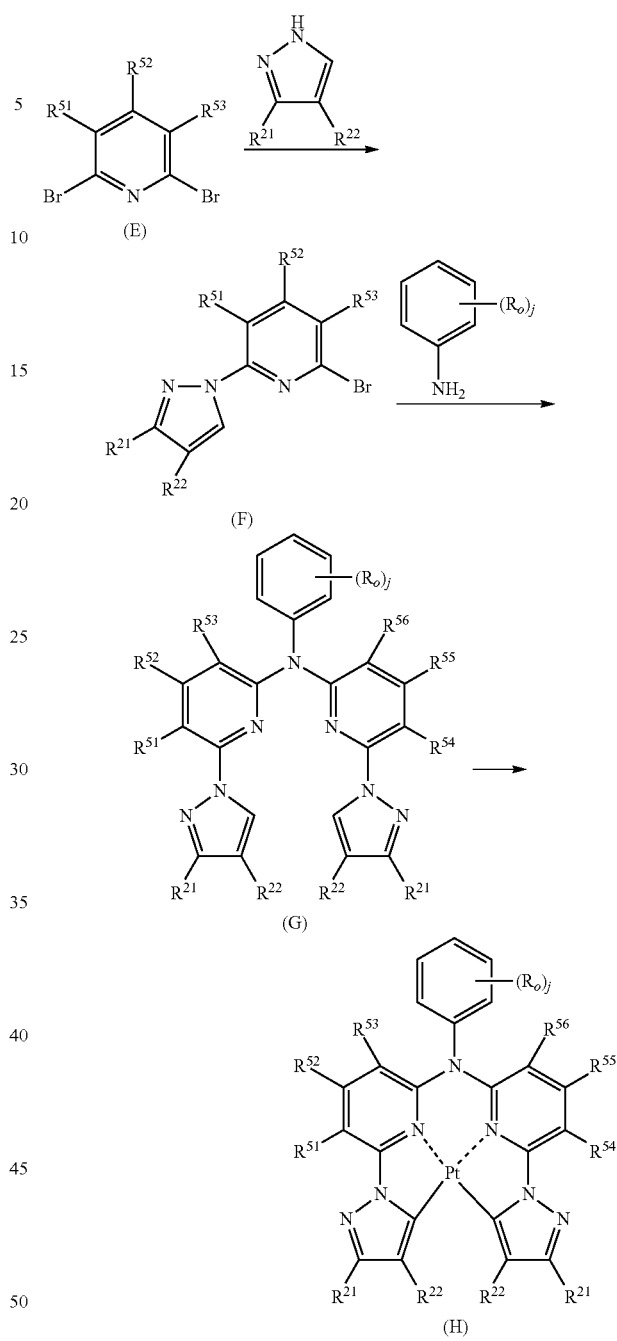

In the above formulae, $R^{21}$, $R^{22}$, $R^{51}$, $R^{52}$, $R^{53}$, $R^{54}$ and $R^{55}$ each independently represents a hydrogen atom or a substituent. $R_O$ represents a substituent. j represents an integer of from 0 to 5.

The step of obtaining the compound (F) from the compound (E) can be conducted according to the method described in *Journal of Organic Chemistry*, 56, 12, 4072-4074 (1980), to thereby synthesize the compound (F).

The step of obtaining the compound (G) from the compound (F) can be conducted according to the method described in *Angew. Chem. Int. Ed*, 42, 2051-2053 (2003), to thereby synthesize the compound (F).

The step of obtaining the compound (H) of the invention from the compound (G) can be conducted by dissolving the compound (G) and 1 to 1.5 equivalents of platinous chloride in benzonitrile, heating to 130° C. to a reflux temperature (boiling point of benzonitrile: 191° C.) for 30 minutes to 24 hours under stirring. The compound (H) can be purified by recrystallization using chloroform or ethyl acetate, by silica gel column chromatography or by sublimation purification.

Additionally, in the above-described production process, when the defined substituent would undergo change under a certain synthesizing condition or is not suitable for performing the process, the compound containing such substituent can easily be produced by applying the technique of protecting the functional group and removing the protective group according to, for example, *Protective Groups in Organic Synthesis*, written by T. W. Green and published by John Wiley & Sons Inc. in 1981. Also, the order of the reaction steps of introducing the substituent can properly be changed, as needed.

<Synthesis Example>
(1) Synthesis of Illustrative Compound 2

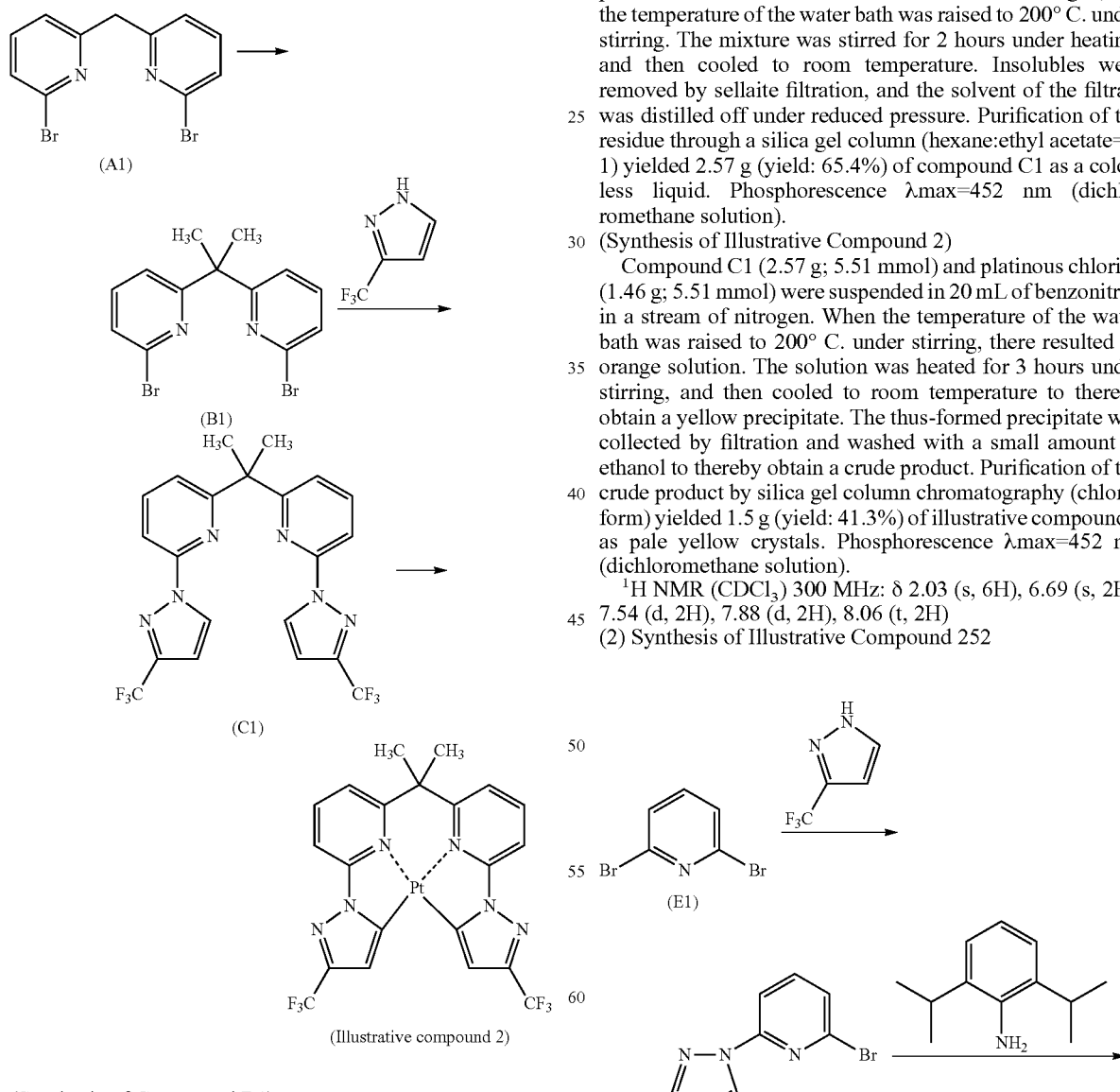

(Synthesis of Compound B1)
Compound A1 (18.6 g) was dissolved in 90 mL of N,N-dimethylformamide in a stream of nitrogen, the resulting solution was cooled to 0° C., potassium t-butoxide (6.8 g; 1.05 equivalents) was added thereto, and the temperature of the mixture was raised to room temperature, followed by stirring for 30 minutes. The mixture was again cooled to 0° C., methyl iodide (7.2 mL; 1.82 equivalents) was added thereto, and the temperature was raised to room temperature, followed by stirring for 30 minutes to conduct monomethylation. This procedure was repeated to conduct dimethylation. The reaction product was extracted with ethyl acetate, washed with successive, water and a saturated sodium chloride aqueous solution. Then, the organic layer was dried over magnesium sulfate, and ethyl acetate was distilled off. A crude product thus obtained was purified by silica gel column chromatography (hexane:ethyl acetate=20:1) to thereby obtain 18.6 g (yield: 92.1%) of compound B1 as colorless crystals.

(Synthesis of Compound C1)
Compound B1 (3 g; 8.43 mmol), 3-trifluoromethylpyrazole (3.44 g; 25.28 mmol), potassium carbonate (7 g; 50.58 mmol) and copper iodide (322 mg; 1.69 mmol) were suspended in 50 mL of nitrobenzene in a stream of nitrogen, and the temperature of the water bath was raised to 200° C. under stirring. The mixture was stirred for 2 hours under heating, and then cooled to room temperature. Insolubles were removed by sellaite filtration, and the solvent of the filtrate was distilled off under reduced pressure. Purification of the residue through a silica gel column (hexane:ethyl acetate=9:1) yielded 2.57 g (yield: 65.4%) of compound C1 as a colorless liquid. Phosphorescence λmax=452 nm (dichloromethane solution).

(Synthesis of Illustrative Compound 2)
Compound C1 (2.57 g; 5.51 mmol) and platinous chloride (1.46 g; 5.51 mmol) were suspended in 20 mL of benzonitrile in a stream of nitrogen. When the temperature of the water bath was raised to 200° C. under stirring, there resulted an orange solution. The solution was heated for 3 hours under stirring, and then cooled to room temperature to thereby obtain a yellow precipitate. The thus-formed precipitate was collected by filtration and washed with a small amount of ethanol to thereby obtain a crude product. Purification of the crude product by silica gel column chromatography (chloroform) yielded 1.5 g (yield: 41.3%) of illustrative compound 2 as pale yellow crystals. Phosphorescence λmax=452 nm (dichloromethane solution).

$^1$H NMR (CDCl$_3$) 300 MHz: δ 2.03 (s, 6H), 6.69 (s, 2H), 7.54 (d, 2H), 7.88 (d, 2H), 8.06 (t, 2H)

(2) Synthesis of Illustrative Compound 252

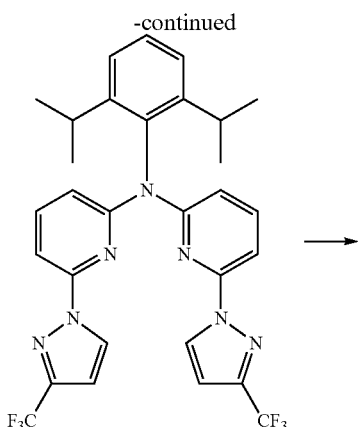

(G1)

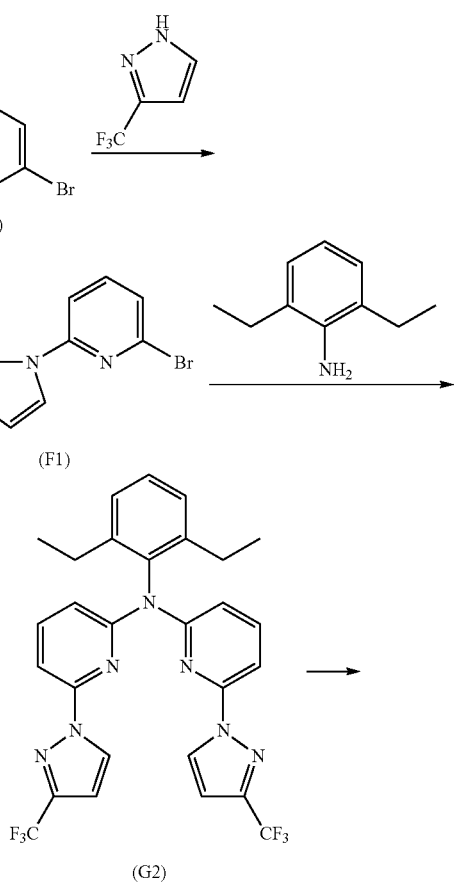

(Illustrative compound 252)

(Synthesis of Compound F1)

2,6-dibromopyridine (Compound E1; 28.42 g, 120 mmol), 3-trifluoromethylpyrazole (4.08 g; 30 mmol), copper I oxide (0.21 g, 1.5 mmol), salicyl aldoxime (0.82 g, 6 mm) and cesium carbonate (19.55 g, 60 mmol) were suspended in 90 mL of N,N-dimethylformamide in a stream of nitrogen, and the resulting solution was refluxed for 5.5 hours under stirring to provide a reaction product. After standing to cool, water was added to the reaction product, and the resulting solution was extracted with ethyl acetate to concentrate the organic layer. The residue thus obtained was purified by silica gel column chromatography (hexane:ethyl acetate=95:5) to thereby obtain 5.2 g (yield: 59%) of compound F1 as crystals.

$^1$H NMR (CDCl$_3$) 300 MHz: δ 6.72 (d, J=2.7 Hz, 1H), 7.45 (d, J=7.8 Hz, 1H), 7.71 (t, J=8.0 Hz, 1H), 7.99 (d, J=8.1 Hz, 1H), 8.59-8.69 (m, 1H)

(Synthesis of Compound G1)

π-allylpalladium chloride dimmer (di-μ-chlorobis(η-allyl) palladium(II)) (2.78 mg, 7.6×10$^{-3}$ mmol), hexane solution of 10 weight % tri-t-butylphosphine (3.0 g corresponding to the amount of tri-t-butylphosphine, 0.15×10$^{-3}$ mmol) and 6 ml of xylene were stirred at a room temperature. To the obtained solution, sodium t-butoxide (0.19 g, 2.0 mmol), 2,5-diisopropylaniline (0.17 g, 1.0 mmol) and compound F1 (0.6 g, 2.0 mmol) was add, and the resulting solution was refluxed for 16.5 hours to provide a reaction product. After standing to cool, water was added to the reaction product, and the resulting solution was extracted with ethyl acetate to concentrate the organic layer, to thereby obtain 0.43 g of crude compound G1.

(Synthesis of Illustrative Compound 252)

Crude compound G1 (0.43 g), platinum chloride (0.25 g, 0.93 mmol) and 5 ml of benzonitrile were stirred for 17 hours in a stream of nitrogen while gradually raising the temperature from 120° C. to 180° C. After standing to cool, benzonitrile was distilled away, and the resulting solution was purified by silica gel column chromatography (chloroform: hexane=1:1) to thereby obtain 10 mg (yield: 5%) of illustrative compound 252. Phosphorescence λmax=444 nm (dichloromethane solution).

$^1$H NMR (CDCl$_3$) 300 MHz: δ 1.01 (d, 12H), 2.65 (sep, 2H), 6.34 (d, J=9.3 Hz, 2H), 6.76 (s, 2H), 7.53 (d, J=7.5 Hz, 2H), 7.68-7.74 (m, 3H), 7.68-7.92 (m, 2H)

(3) Synthesis of Illustrative Compound 251

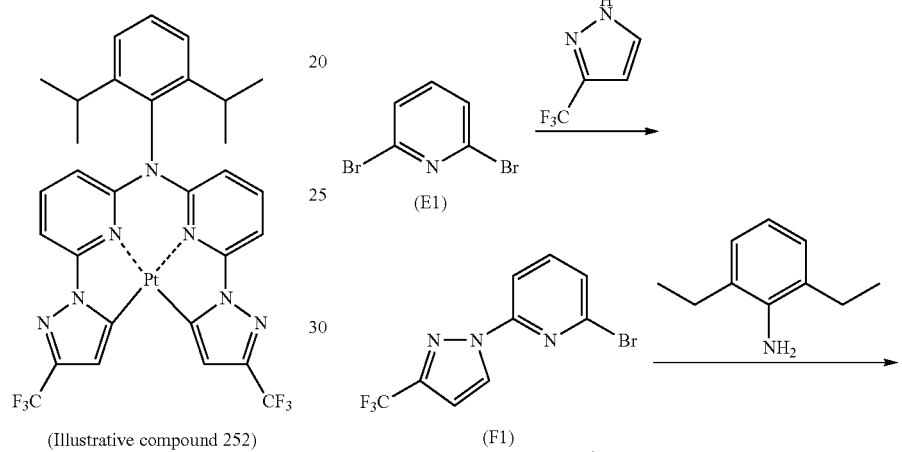

(E1)

(F1)

(G2)

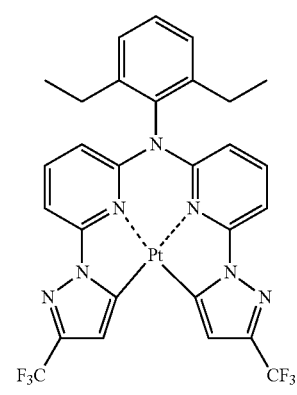

(Illustrative compound 251)

(Synthesis of Compound G2)

Bis(benzylidene acetone)palladium (0.16 g, 0.28 mmol), 2,2'-bis(diphenylphosphino)-1,1'-binaphthyl (0.17 g, 21 mmol) and 30 ml of toluene were stirred at a room temperature. To the obtained solution Sodium t-butoxide 2.01 g, 21 mmol), 2,5-diethylaniline (1.05 g, 7 mmol) and compound F1 (4.2 g, 14.5 mmol) was add, and the resulting solution was refluxed for 8 hours to provide a reaction product. After standing to cool, water was added to the reaction product, and the resulting solution was extracted with ethyl acetate to concentrate the organic layer, to thereby obtain 1.01 g of crude compound G2.

(Synthesis of Illustrative Compound 251)

Crude compound G1 (1.01 g), platinum chloride (0.64 g, 2.4 mmol) and 25 ml of benzonitrile were stirred for 8 hours in a stream of nitrogen while gradually raising the temperature from 120° C. to 180° C. After standing to cool, benzonitrile was distilled away, and the resulting solution was purified by silica gel column chromatography (chloroform: hexane=1:1) to thereby obtain 0.21 g (yield: 28%) of illustrative compound 251. Phosphorescence λmax=444 nm (dichloromethane solution).

$^1$H NMR (CDCl$_3$) 300 MHz: δ 1.05 (t, 6H), 2.34 (m, 4H), 6.32 (d, 2H), 6.75 (s, 2H), 7.51 (d, 2H), 7.65 (t, 1H), 7.70 (d, 2H), 7.88 (d, 2H)

(4) Synthesis of Illustrative Compound 254

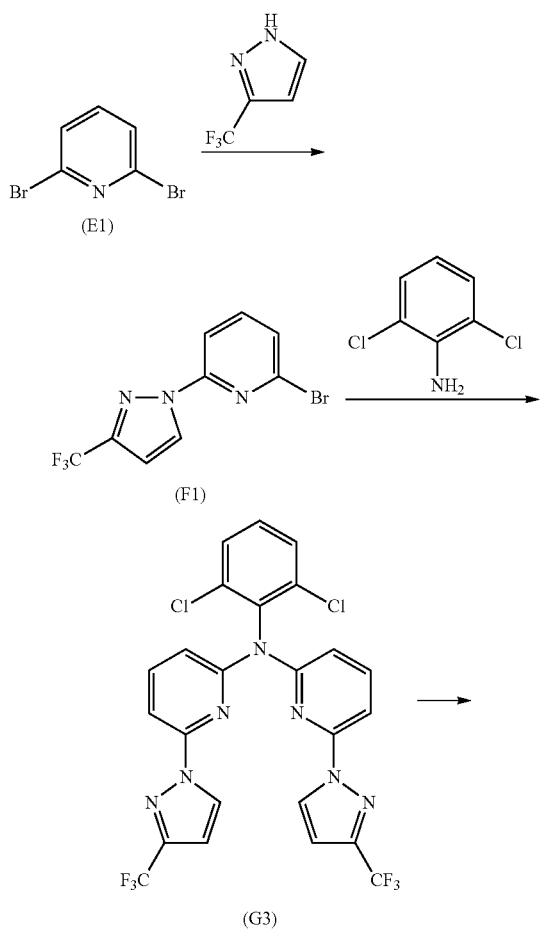

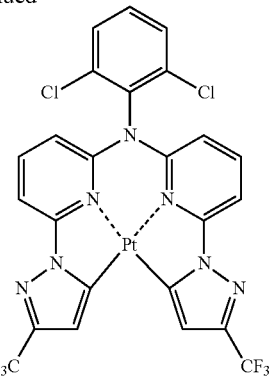

(Illustrative Compound 254)

(Synthesis of Compound G3)

Bis(benzylidene acetone)palladium (85 mg, 0.15 mmol), 2,2'-bis(diphenylphosphino)-1,1'-binaphthyl (92 mg, 0.15 mmol) and 15 ml of toluene were stirred at a room temperature. To the obtained solution, sodium t-butoxide (1.42 g, 15 mmol), 2,5-dichloroaniline (0.6 g, 3.7 mmol) and compound F1 (3.2 g, 11.1 mmol) was add, and the resulting solution was refluxed for 24 hours to provide a reaction product. After standing to cool, water was added to the reaction product, and the resulting solution was extracted with ethyl acetate to concentrate the organic layer. The residue thus obtained was purified by silica gel column chromatography (hexane:ethyl acetate=95:5) to thereby obtain 1.13 g (yield: 52%) of compound G3 as crystals.

$^1$H NMR (CDCl$_3$) 300 MHz: δ 6.60 (s, 2H), 7.13 (d, 2H), 7.40 (t, 1H), 7.52 (d, 2H), 7.68 (d, 2H), 7.79 (t, 2H), 8.11 (s, 2H)

(Synthesis of Illustrative Compound 254)

Crude compound G3 (0.68 g, 1.1 mmol), platinum chloride (0.29 g, 1.1 mmol) and 30 ml of benzonitrile were stirred for 8 hours in a stream of nitrogen while gradually raising the temperature from 120° C. to 180° C. After standing to cool, benzonitrile was distilled away, and the resulting solution was purified by silica gel column chromatography (chloroform) to thereby obtain 0.15 g (yield: 16%) of illustrative compound 254.

$^1$H NMR (CDCl$_3$) 300 MHz: δ 6.27 (d, 2H), 6.62 (s, 2H), 7.65-7.78 (m, 5H), 7.92 (t, 2H)

m/z=778 (M+H)

The invention will be described in more detail by reference to Examples which, however, are not construed as limiting the invention.

<Organic Electroluminescent Device>

1. Preparation of Organic Electroluminescent Device (1) Preparation of Organic Electroluminescent Device of the Invention (TC-21)

A 0.5-mm thick, 2.5-cm square glass substrate having an ITO film (manufactured by GEOMATEC Company Limited; surface resistance: 10□/Ω) was placed in a washing container, and was washed in 2-propanol by applying ultrasonic waves, followed by UV-ozone treatment for 30 minutes. On this transparent anode (ITO film) were successively vacuum deposited the following organic compound layers by the vacuum deposition method.

The vacuum deposition rate in Examples of the invention is 0.2 nm/second unless otherwise specified. The vacuum deposition rate was measured by using a quartz oscillator. The film thickness described below was also measured by using the quartz oscillator.

(First Hole Transporting Layer)
  Copper phthalocyanine (CuPc): film thickness: 10 nm
(Second Hole Transporting Layer)
  NPD: film thickness: 40 nm
(Light-Emitting Layer)
  A mixture layer of 92% by weight of MCP and 8% by weight of illustrative compound 2: film thickness: 30 nm
(First Electron Transporting Layer)
  1,3,5-TTB: film thickness: 10 nm
(Second Electron Transporting Layer)
  1,3,5-TPB: film thickness: 10 nm
(Third Electron Transporting Layer)
  Alq: film thickness: 10 nm

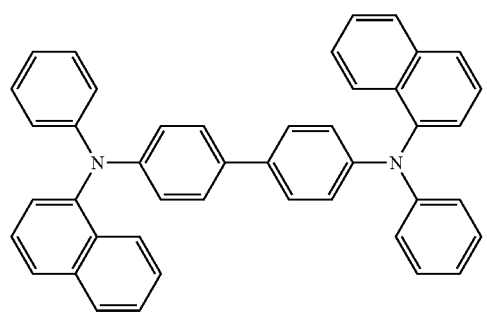

NPD

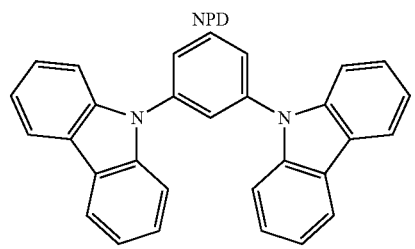

MCP

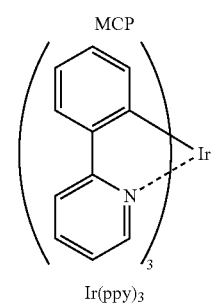

Ir(ppy)₃

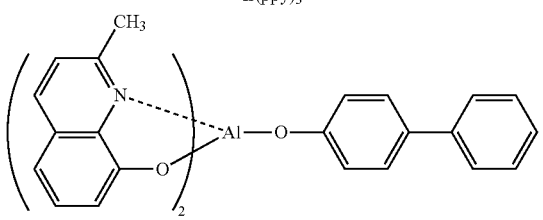

Balq

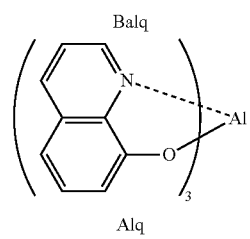

Alq

-continued

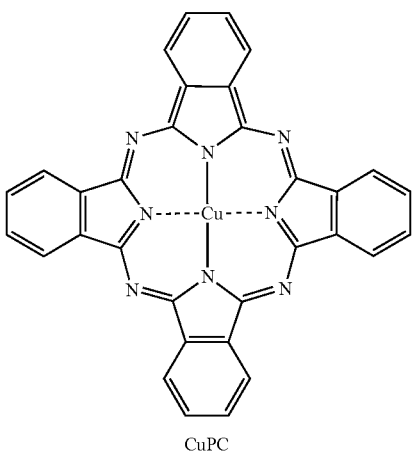

CuPC

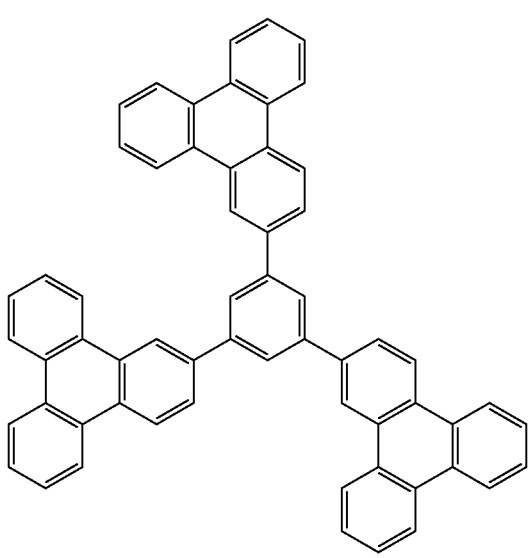

1,3,5-TTB

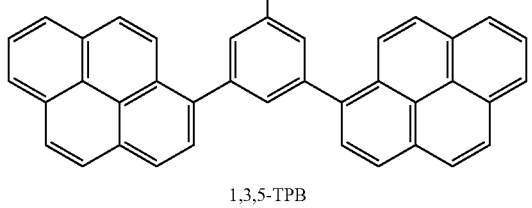

1,3,5-TPB

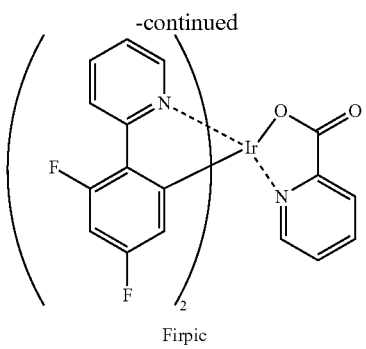

Firpic

Finally, 0.1 nm of lithium fluoride and 100 nm of metallic aluminum were vacuum deposited thereon in this order to form a cathode. The product was placed in an argon gas-replaced globe box without exposing to the atmosphere, and then sealed using a stainless steel-made sealing can and a UV ray-curable adhesive (XNR5516HV; manufactured by Nagase Ciba K.K.) to obtain an organic electroluminescent device (TC-21) as an example of the invention.

(2) Preparation of an Organic Electroluminescent Device (TC-22) for Comparison

An organic electroluminescent device (TC-22) for comparison was prepared in the same manner as with TC-21 except for changing the light-emitting material from the pyrazole-containing compound of the invention to Firpic.

2. Evaluation of the Organic Electroluminescent Devices

The organic electroluminescent devices (TC-21 to 22) obtained above were evaluated in the following manner.

(1) Measurement of the Spectrum of Emitted Light and the External Quantum Effect When a voltage of 11V was applied to the organic electroluminescent devices (TC-21 to 22), both elements emitted blue light originating from the phosphorescent light-emitting materials. Each of these elements was mounted on an emission spectrum-measuring system (ELS1500) manufactured by Shimadzu Corporation, and an emission spectrum at 100 Cd/m² in luminance was measured to determine the peak wavelength of the emitted light. An external quantum effect was obtained from an emission spectrum and current value at 200 Cd/m².

(2) Evaluation of Driving Durability

Each of the obtained organic electroluminescent devices (TC-21 to 22) was mounted on an OLED test system model ST-D manufactured by Tokyo System Development Co., Ltd., and was driven under the condition of constant-current mode and 0.4 mA in a positive-direction constant current to determine the half-value period of luminance (period required for luminance to be reduced to 50% of the initial luminance), $t_{0.5}$. The results thus obtained are shown in Table 1.

TABLE 1

| Element No. | Peak Wavelength of Emitted Light | External Quantum Effect | $t_{0.5}$ | Note |
|---|---|---|---|---|
| TC-21 | 459 nm | 6.1% | 35 hours | Present Invention |
| TC-22 | 466 nm | 2.8% | 15 hours | Comparative Example |

It is seen from the above results that the compound of the invention can provide an organic electroluminescent device showing high light-emitting efficiency and high durability.

It found that other compounds of the invention can provide an organic electroluminescent device showing high light-emitting efficiency and high durability, as the above results.

It will be apparent to those skilled in the art that various modifications and variations can be made to the described embodiments of the invention without departing from the spirit or scope of the invention. Thus, it is intended that the invention cover all modifications and variations of this invention consistent with the scope of the appended claims and their equivalents.

The present application claims foreign priority based on Japanese Patent Application Nos. JP2005-75340, JP2005-75341 and JP2005-171031, filed Mar. 16, Mar. 16 and Jun. 10 of 2005, respectively, the contents of which are incorporated herein by reference.

The invention claimed is:

1. A compound represented by formula (IIA):

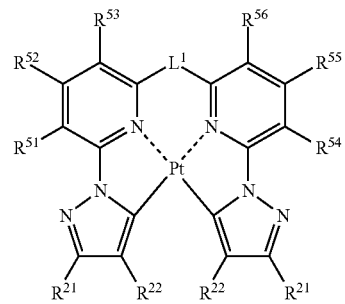

wherein $L^1$ represents a group selected from the group consisting of

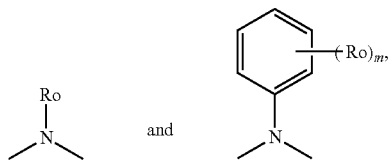

wherein $R_0$ is selected from the group consisting of an alkyl group containing from 1 to 20 carbon atoms, an alkenyl group containing from 2 to 10 carbon atoms, an aryl group containing from 6 to 20 carbon atoms, an amino group containing from 0 to 20 carbon atoms, an alkoxy group containing from 1 to 20 carbon atoms, an aryloxy group containing from 6 to 20 carbon atoms, an acyl group containing from 1 to 20 carbon atoms, an alkoxycarbonyl group containing from 2 to 20 carbon atoms, an alkylthio group containing from 1 to 20 carbon atoms, a sulfonyl group containing from 1 to 20 carbon atoms, a hydroxyl group, a halogen atom, a cyano group, a nitro group and a 5- to 7-membered hetero ring group, and m represents an integer of from 1 to 5, and $R^{21}$, $R^{22}$, $R^{51}$, $R^{52}$, $R^{53}$, $R^{54}$, $R^{55}$ and $R^{56}$ each independently represents a hydrogen atom or a substituent.

2. The compound as described in claim 1, wherein the substituent is one selected from the group consisting of an alkyl group containing from 1 to 20 carbon atoms, an alkenyl group containing from 2 to 10 carbon atoms, an aryl group containing from 6 to 20 carbon atoms, an amino group containing from 0 to 20 carbon atoms, an alkoxy group containing from 1 to 20 carbon atoms, an aryloxy group containing from 6 to 20 carbon atoms, an acyl group containing from 1 to 20 carbon atoms, an alkoxycarbonyl group containing from 2 to 20 carbon atoms, an alkylthio group containing from 1 to 20 carbon atoms, a sulfonyl group containing from 1 to 20 carbon atoms, a hydroxyl group, a halogen atom, a cyano group, a nitro group and a 5- to 7-membered hetero ring group.

3. An organic electroluminescent device comprising:
a pair of electrodes; and
at least one organic layer between the pair of electrodes, the at least one organic layer containing a compound represented by formula (II):

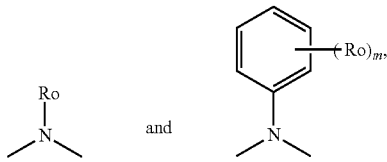

wherein $Z^1$ and $Z^2$ each independently represents a nitrogen-containing aromatic 6-membered ring coordinating to platinum atom at the nitrogen atom thereof,
$L^1$ represents a group selected from the group consisting of

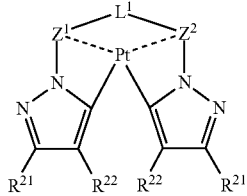

wherein $R_0$ is selected from the group consisting of an alkyl group containing from 1 to 20 carbon atoms, an alkenyl group containing from 2 to 10 carbon atoms, an aryl group containing from 6 to 20 carbon atoms, an amino group containing from 0 to 20 carbon atoms, an alkoxy group containing from 1 to 20 carbon atoms, an aryloxy group containing from 6 to 20 carbon atoms, an acyl group containing from 1 to 20 carbon atoms, an alkoxycarbonyl group containing from 2 to 20 carbon atoms, an alkylthio group containing from 1 to 20 carbon atoms, a sulfonyl group containing from 1 to 20 carbon atoms, a hydroxyl group, a halogen atom, a cyano group, a nitro group and a 5- to 7-membered hetero ring group, and m represents an integer of from 1 to 5, and
$R^{21}$ and $R^{22}$ each independently represents a hydrogen atom or a substituent.

4. The organic electroluminescent device as described in claim 3, wherein the formula (II) is represented by formula (IIA):

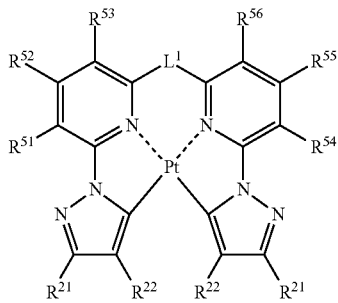

wherein $L^1$ is as defined in formula (II), and $R^{21}$, $R^{22}$, $R^{51}$, $R^{52}$, $R^{53}$, $R^{54}$, $R^{55}$ and $R^{56}$ each independently represents a hydrogen atom or a substituent.

5. The organic electroluminescent device as described in claim 3 or 4, wherein the substituent is a substituent selected from the group consisting of an alkyl group containing from 1 to 20 carbon atoms, an alkenyl group containing from 2 to 10 carbon atoms, an aryl group containing from 6 to 20 carbon atoms, an amino group containing from 0 to 20 carbon atoms, an alkoxy group containing from 1 to 20 carbon atoms, an aryloxy group containing from 6 to 20 carbon atoms, an acyl group containing from 1 to 20 carbon atoms, an alkoxycarbonyl group containing from 2 to 20 carbon atoms, an alkylthio group containing from 1 to 20 carbon atoms, a sulfonyl group containing from 1 to 20 carbon atoms, a hydroxyl group, a halogen atom, a cyano group, a nitro group and a 5- to 7-membered hetero ring group.

* * * * *